United States Patent [19]
Tait et al.

[11] Patent Number: 6,103,761
[45] Date of Patent: Aug. 15, 2000

[54] AGENTS ACTING AT CHOLECYSTOKININ RECEPTORS

[75] Inventors: Bradley Dean Tait, Canton; Michael William Wilson, Ann Arbor, both of Mich.

[73] Assignee: Warner-Lambert Company, Morris Plains, N.J.

[21] Appl. No.: 08/325,852

[22] Filed: Oct. 19, 1994

Related U.S. Application Data

[60] Division of application No. 08/118,374, Sep. 13, 1993, Pat. No. 5,389,682, which is a continuation-in-part of application No. 07/947,234, Sep. 18, 1992, abandoned.

[51] Int. Cl.$^7$ .......................... A61K 31/17; A61K 31/18; A61K 31/275; A61K 31/40
[52] U.S. Cl. .......................... 514/522; 514/255; 514/256; 514/332; 514/414; 514/419; 514/524; 514/539; 514/562; 514/564; 514/586; 514/588; 514/592; 514/593; 514/595; 514/596; 514/597; 514/598; 544/296; 544/357; 546/265
[58] Field of Search .......................... 564/27, 39, 40, 564/42, 48, 49, 50, 51, 52, 53, 54, 56, 57; 558/412, 414; 514/522, 524, 586, 419, 539, 562, 564, 588, 592, 593, 595, 596, 597, 598; 548/495; 560/27, 29, 430, 439

[56] References Cited

U.S. PATENT DOCUMENTS

| 5,384,425 | 1/1995 | Ito et al. ................................. 560/138 |
| 5,389,682 | 2/1995 | Tait et al. ................................ 514/592 |

FOREIGN PATENT DOCUMENTS

| 0250148 | 12/1987 | European Pat. Off. . |
| 91/13862 | 9/1991 | WIPO . |

OTHER PUBLICATIONS

Weir et al., Chem. Abst. 88:120771, 1978.
Schick, Yaksh, Go. *Regulatory Peptides* 1986; 14: 277–91.
Hill, Hughes, Pittaway. *Neuropharmacology* 1987; 26: 289–300.
MacVicar, Kerrin, Davison. *Brain Research* 1987; 406: 130–5.
Roberts, Ferrier, Lee, et. al. *Brain Research* 1983; 288: 199–211.
Totterdell, Smith. *Neuroscience* 1986; 19: 181–92.
Weiss, Tanzer, Ettenberg. *Pharmacology, Biochemistry, and Behavior* 1988; 30: 309–317.
Schneider, Alpert, Iversen. *Peptides* 1983; 4:749–53.
Konturek. *Gastrointestinal Hormones* 1980; 23:529–64, ed. G.B.J. Glass, Raven Press, NY.
Johnson, *ibid*. pp. 507–527.
Stadil, *ibid*. pp. 729–739.
Singh, Walker, Townsend, Thompson. *Cancer Research* 1986; 46: 1612–16.
Dockray, GJ. *British Med Bull* 1982; 38(3): 253–8.
Morley, JE. *Life Science* 1980; 27: 355–68.
Rehfeld, Gotterman. *J. Neurochem* 1979; 32: 1339–41.
Della–Fera, Baile. *Science* 1979; 206: 471–3.
Demeulemeester, H, et.al. *J. Neuroscience* 1988; 8: 988–1000.
*Tips* 1990; 11: 271–273.
Corey, EJ. et.al. *J Am Chem Soc* 1989; 111: 5493–5 and Supplementary Material.
Williams, Of, et.al. *J. Am Chem Soc* 1959; 81: 4464–9.
Saigo, K. et.al. *Bull Chem Soc Japan* 1986; 59: 931–2.
Gust, R. et al. *J. Med. Chem.* 1990; 33: 2535–44.
Smith, J. et al. *Gastroenterology* 1988; 95: 1541–8.
Mutt. *Gastrointestinal Hormones* pp. 169–221.
Harvey, S.C. *The Pharmacological Basis of Therapeutics* 7th ed., 1985; 339–71.
M. Brana, et al., *J. of Het. Chem.*, vol. 24,No. 2, 1987, 369–371.
Y. Dobashi, et al., *J. Org. Chem*, vol. 52, No. 12, 1987, 2490–2496.
J. Cristol, et al., *J. Org. Chem.*, vol. 42, No 14, 1977, 2378–2379.
V. Mutt, *Gastrointestinal Hormones*, G.B. Glass, Ed., Raven Press, New York, 1980, 169–221.

*Primary Examiner*—Peter O'Sullivan
*Attorney, Agent, or Firm*—Elizabeth M. Anderson

[57] ABSTRACT

The invention concerns a series of novel bis-urea derivatives, nonpeptides, which show good binding affinity for the CCK-B receptor. The compounds, compositions containing them, methods of preparation, and utilities including anxiety, gastric acid secretion inhibition, and psychoses are included.

13 Claims, No Drawings

AGENTS ACTING AT CHOLECYSTOKININ RECEPTORS

This is a Divisional application of U.S. Ser. No. 08/118,374 filed Sep. 13, 1993, now U.S. Pat. No. 5,389,682, which is a Continuation-In-Part application of U.S. Ser. No. 07/947,234, filed Sep. 18, 1992, now abandoned.

BACKGROUND OF THE INVENTION

Agents acting at central cholecystokinin (CCK) receptors may induce satiety (Schick, Yaksh, Go, *Regulatory Peptides* 1986;14:277–91). They are also expected to act as analgesics (Hill, Hughes, Pittaway, *Neuropharmacology* 1987;26:289–300), and as anticonvulsants (MacVicar, Kerrin, Davison, *Brain Research* 1987;406:130–5).

Reduced levels of CCK-peptides have been found in the brains of schizophrenic patients compared with controls (Roberts, Ferrier, Lee, et al., Brain Research 1983;288:199–211). It has been proposed that changes in the activity of CCK neurones projecting to the nucleus accumbens may play a role in schizophrenic processes by influencing dopaminergic function (Totterdell, Smith, *Neuroscience* 1986;19:181–92). This is consistent with numerous reports that CCK peptides modulate dopaminergic function in the basal ganglia and particularly the nucleus accumbens (Weiss, Tanzer, Ettenberg, *Pharmacology, Biochemistry and Behaviour* 1988;30:309–17; Schneider, Allpert, Iversen, *Peptides* 1983;4:749–53). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, *Gastrointestinal Hormones* 1980;23:529–64, ed. G. B. J. Glass, Raven Press, NY). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastrointestinal tract (Johnson, ibid., pp 507–527), actions which are associated with increased DNA and RNA synthesis. Moreover, gastrin secreting cells are associated with certain gastrointestinal tumors as in the Zollinger-Ellison syndrome (Stadil, ibid., pp 279–739), and some colorectal tumors may also be gastrin/CCK dependent (Singh, Walker, Townsend, Thompson, *Cancer Research* 1986;46:1612, and Smith J P, *Gastroenterology* 1988;95:1541). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33-amino acid hormone and various carboxyl-terminus fragments of this peptide (e.g., the octapeptide CCK26-33 and the tetrapeptide CCK30-33). (Dockray G J, *Br Med Bull* 1982;38(3):253–8).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions, and other behavioral effects. ("Cholecystokinin: Isolation, Structure, and Functions," G. B. J. Glass, Ed., Raven Press, New York, 1980;169–221; Morley J E, *Life Sciences* 1980;27:355–68; "Cholecystokinin in the Nervous System," de Belleroche J, Dockray G J, Ed., Ellis Horwood, Chichester, England, 1984;110–27.)

The high concentrations of CCK peptides in many brain areas also indicate major brain functions for these peptides (Dockray G J, *Br Med Bull* 1982;38(3):253–8). The most abundant form of brain CCK found is CCK26-33, although small quantities of CCK30-33 exist (Rehfeld, Gotterman, *J Neurochem* 1979;32:1339–41). The role of central nervous system CCK is not known with certainty but it has been implicated in the control of feeding (Della-Fera, Baile, *Science* 1979;206:471–3).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (Demeulemeester H, et al., *J Neuroscience* 1988;8:988–1000). Agents that modify GABA action may have utility as anxiolytic or hypnotic agents (Harvey S C, *The Pharmacological Basis of Therapeutics* (7th ed.) 1985;339–71, MacMillan). Thus, agents which modify CCK action may have parallel anxiolytic or hypnotic activities. The role of CCK in anxiety is disclosed in *TIPS* 1990;11:271–3.

SUMMARY OF THE INVENTION

The invention relates to novel compounds of formula

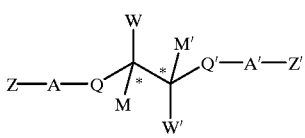

I and the pharmaceutically acceptable salts thereof wherein Z, Z', A, A', Q, Q', M, M', W, and W' are as defined herein.

The invention also relates to a pharmaceutical composition containing a therapeutically effective amount of a compound of Formula I in combination with a pharmaceutically acceptable carrier for appetite suppression in unit dosage.

The invention further relates to a method of appetite suppression in mammals which comprises administering an amount effective to suppress appetite of the composition described above to a mammal in need of such treatment.

The invention also relates to a pharmaceutical composition for reducing gastric acid secretion containing a therapeutically effective amount of a compound of Formula I in combination with a pharmaceutically acceptable carrier effective for reducing gastric acid secretion in unit dosage form.

The invention also relates to a method for reducing gastric acid secretion in mammals which comprises administering an amount effective for gastric acid secretion reduction of the composition described above to a mammal in need of such treatment.

The invention also relates to a pharmaceutical composition containing an effective amount of a compound of Formula I in combination with a pharmaceutically acceptable carrier effective for reducing anxiety in unit dosage form.

The invention also relates to a method for reducing or preventing anxiety in mammals in need of such treatment which comprises administering an amount effective for anxiety reduction of the composition described above to a mammal in need of such treatment.

The invention also relates to a pharmaceutical composition containing an effective amount of a compound of Formula I in combination with a pharmaceutically acceptable carrier effective for treating gastrointestinal ulcers in unit dosage form.

The invention further relates to a method for treating gastrointestinal ulcers in a mammal which comprises administering an amount effective for gastrointestinal ulcer treatment of the composition as described above to a mammal in need of such treatment.

The invention also relates to a pharmaceutical composition containing an effective amount of a compound of Formula I in combination with a pharmaceutically acceptable carrier effective for treating psychosis, i.e., schizophrenia, in unit dosage form.

The invention further relates to a method for treating psychosis in mammals which comprises administering an amount effective for treating psychoses of a composition as described above to a mammal in need of such treatment.

The invention also relates to a pharmaceutical composition effective for stimulating or blocking CCK or gastrin receptors, for altering the activity of brain neurons, for treating disorders of the extrapyramidal motor system, for blocking the trophic and growth stimulating actions of CCK and gastrin, and for treating gastrointestinal motility.

The invention also relates to a pharmaceutical composition for preventing the withdrawal response produced by chronic treatment or abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, alcohol, nicotine, and caffeine. Withdrawal symptoms are treated by administration of an effective withdrawal treating amount of a compound of the instant invention.

Compounds of the invention are also useful as analgesics and in potentiating the effect of morphine. They can be used as an adjunct to morphine and other opioids in the treatment of severe pain such as cancer pain and reduce the dose of morphine in treatment of pain where morphine is contraindicated.

The invention further relates to the use of the compounds of Formula I to prepare pharmaceutical and diagnostic compositions for the treatment and diagnosis of the conditions described above.

The invention further provides processes for the preparation of compounds of Formula I.

The invention further provides novel intermediates useful in the preparation of compounds of Formula I and also provides processes for the preparation of the intermediates.

DETAILED DESCRIPTION

The compounds of the present invention are those of formula

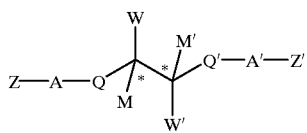

I or a pharmaceutically acceptable salt thereof wherein:

Z and Z' are each independently selected from:
  hydrogen,
  CN,
  alkyl of from 1 to 6 carbon atoms,
  branched alkyl of from 3 to 9 carbon atoms,
  cycloalkyl or polycycloalkyl of from 5 to 12 carbon atoms unsubstituted, mono- or disubstituted with one or more substituents selected from:
    alkyl,
    branched alkyl,
    $CO_2R^1$, and
    —$OR^3$ wherein $R^1$ is as defined below, and
    $R^3$ is
      hydrogen,
      —$CH_3$,
      —$CH_2CH_3$, or
      $C(O)CH_3$.

Unsubstituted, mono- or polysubstituted phenyl, polyaromatic, heteroaromatic, or hydroaromatic which substituents are selected from:
  alkyl of from 1 to 6 carbon atoms,
  branched alkyl of from 3 to 9 carbon atoms,
  hydrogen,
  —CN,
  —SMe,
  —$S(O)_2CF_3$,
  —S(O)Me,
  —$S(O)_2Me$,
  —$(CH_2)_mS(O_2)OR^1$,
  —F,
  —Cl,
  —Br,
  —I
  —$CF_3$,
  —$NO_2$,
  —$S(O)_2NR^1R^2$,
  —CHO,
  —C(NOH)H,
  —$(CH_2)_mCO_2R^1$,
  —$C(O)NR^1R^2$,
  —$NR^1R^2$,
  —$C(O)CO_2R^1$,
  —$C(NOH)CO_2R^1$,
  —$OR^1$,
  —OAc,

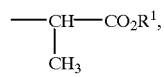

-continued $$-CH(CH_3)-SO_3R^1$$

wherein $R^1$ and $R^2$ are as defined below.

[tetrazole structure], and [thiadiazole-2-thione structure];

A' is a bond, $$-(CH_2)_m-C(O)-NY'-(CH_2)_n-,$$

$$-(CH_2)_m-C(S)-NY'-(CH_2)_n-,$$

$$-(CH_2)_m-C(=NCN)-O-(CH_2)_n-,$$

$$-(CH_2)_m-C(=NH)-O-(CH_2)_n-,$$

$$-(CH_2)_m-C(=NCN)-NY'-(CH_2)_n-,$$

$$-(CH_2)_m-C(=NNO_2)-NY'-(CH_2)_n-,$$

$$-(CH_2)_m-C(=NH)-NY'-(CH_2)_n-,$$

$$-(CH_2)_m-C(O)-NY'-SO_2(CH_2)_n-,$$

$$-(CH_2)_m-C(S)-(CH_2)_n-,$$

$$-(CH_2)_m-C(O)-(CH_2)_n-,$$

$$-(CH_2)_m-S(O)_2-(CH_2)_n-,$$

$$-(CH_2)_m-S(O)_2-NY'-(CH_2)_n-,$$

$$-(CH_2)_m-C(S)-NY'SO_2-(CH_2)_n-,$$

$$-(CH_2)_m-C(O)-O-(CH_2)_n-, \text{ or } -(CH_2)_n-$$

wherein m and n are each independently an integer of from 0 to 3.

A is a bond, $$-(CH_2)_m-NY-C(O)-(CH_2)_n-,$$

$$-(CH_2)_m-NY-C(S)-(CH_2)_n-,$$

$$-(CH_2)_m-O-C(=NCN)-(CH_2)_n-,$$

$$-(CH_2)_m-O-C(=NH)-(CH_2)_n-,$$

$$-(CH_2)_m-NY-C(=NCN)-(CH_2)_n-,$$

$$-(CH_2)_m-NY-C(=NNO_2)-(CH_2)_n-,$$

$$-(CH_2)_m-NY-C(=NH)-(CH_2)_n-,$$

$$-(CH_2)_m-SO_2-NY-C(O)-(CH_2)_m-,$$

$$-(CH_2)_m-C(S)-(CH_2)_n-,$$

$$-(CH_2)_m-C(O)-(CH_2)_n-,$$

$$-(CH_2)_m-S(O)-(CH_2)_n-,$$

$$-(CH_2)_m-NY-S(O)_2-(CH_2)_n-,$$

$$-(CH_2)_m-SO_2NY-C(S)-(CH_2)_n-,$$

$$-(CH_2)_m-O-C(O)-(CH_2)_n-, \text{ or } -(CH_2)_n-$$

wherein m and n are as defined above.

Q and Q' are each independently NY, NY', or oxygen wherein Y and Y' are each independently:
hydrogen,
phenyl,
benzyl,
straight alkyl of from 1 to 4 carbon atoms,
branched alkyl of 3 or 4 carbon atoms,
—$(CH_2)_nCO_2R^1$, or
—$(CH_2)_n$—$C(O)NR^1R^2$;

W and W' are each independently:
phenyl which is unsubstituted, mono- or polysubstituted by:
hydrogen,
—CN,
—SMe,
—$SO_2CF_3$,
—S(O)Me,
—$S(O)_2Me$,
—$(CH_2)_mS(O)_2OR^1$,
—$S(O)_2NR^1R^2$,
—CHO,
—C(NOH)H,
—$(CH_2)_mCO_2R^1$,
—$C(O)NR^1R^2$,
—$NR^1R^2$, —(CO)CO$_2$R$^1$,
—C(NOH)CO$_2$R$^1$,
—OR$^1$,
—OAc,

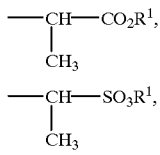

—F,
—Br,
—Cl,
—I,
—CF$_3$,
—NO$_2$,
alkyl of from 1 to 6 carbon atoms,
branched alkyl of from 3 to 9 carbon atoms,

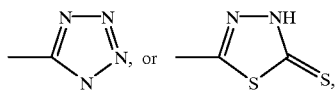

Also, W and W' are each independently:

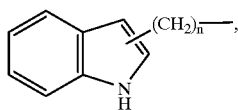

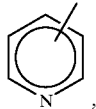

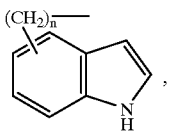

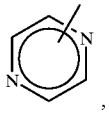

cyclo or polycycloalkyl unsubstituted or substituted by one or more selected from alkyl, CO$_2$R$^1$, and —S(O)$_2$OR$^1$;
M and M' are each independently hydrogen, methyl, or fluorine;
R$^1$ and R$^2$ are each independently hydrogen or lower alkyl;
R$^3$ is hydrogen, methyl, ethyl, or C(O)CH$_3$;
m and n are each independently an integer of from 0 to 3;
with the proviso that when Z and Z' are both hydrogen and A and A' are both a bond, Y and Y' are not both hydrogen,
with the further proviso that when Q and Q' are both oxygen and A and A' are both bonds, Z and Z' are not both hydrogen,
with the further proviso that when Z and Z' are both hydrogen, and A and A' are both a bond when Q is oxygen and Q' is NY' or Q' is oxygen and Q is NY, Y' or Y are not hydrogen.

Known compounds 1,2-diphenyl-ethane-1,2-diamine, 1,2-diphenyl-ethane-1,2-diol, and 2-amino-1,2-diphenyl ethanol are not included in Formula I.

Preferred compounds of the instant invention are those of Formula I wherein:

Z and Z' are each independently selected from:
  hydrogen,
  cyclo- or polycycloalkyl of from 5 to 12 carbon atoms unsubstituted, mono- or disubstituted with substituents selected from:
    alkyl,
    CO$_2$R$^1$, or
    —OR$^3$ wherein R$^3$ is
      hydrogen,
      CH$_3$,
      CH$_2$CH$_3$, or
      C(O)CH$_3$.

Unsubstituted, mono- or disubstituted phenyl which substituents are selected from:
  hydrogen,
  —I,
  —F,
  —Cl,
  —Br,
  —CF$_3$,
  —NO$_2$,
  alkyl of from 1 to 6 carbon atoms,
  branched alkyl of from 3 to 9 carbon atoms
  —CN,
  —SMe,
  —S(O)Me,
  —S(O)$_2$Me,
  —(CH$_2$)$_m$S(O)$_2$OR$^1$,
  —SO$_2$CF$_3$,
  —S(O)$_2$NR$^1$R$^2$,
  —CHO,
  —C(NOH)H,
  —(CH$_2$)$_m$CO$_2$R$^1$,
  —C(O)NR$^1$R$^2$,
  —NR$^1$R$^2$,
  —C(O)CO$_2$R$^1$,
  —(NOH) CO$_2$R$^1$,
  —OR$^1$,
  —OAc,

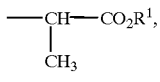

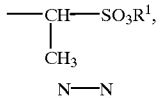

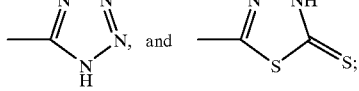

wherein R$^1$ and R$^2$ are each independently hydrogen or lower alkyl.

A' is:

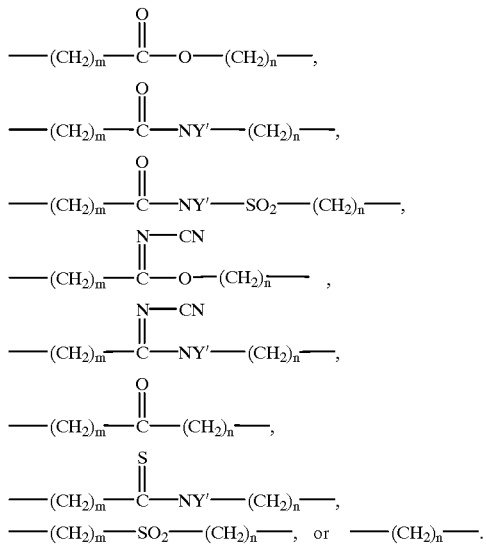

A is:

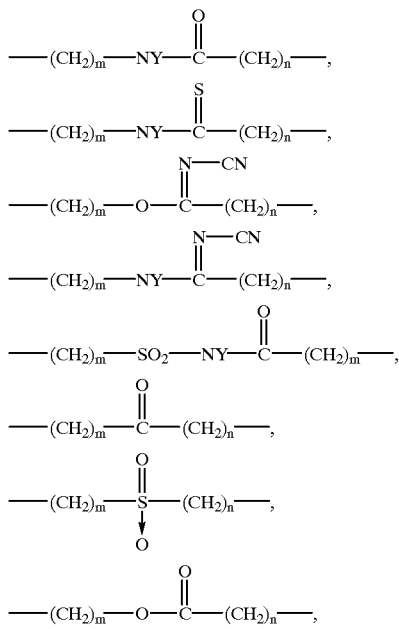

or —$(CH_2)_n$— wherein independently m is from 0 to 1 and independently n is from 0 to 1.

Q and Q' are each independently NY, NY', or oxygen wherein Y and Y' are each independently:
hydrogen,
methyl,
benzyl,
isopropyl,
isobutyl,
sec-butyl,
—$CH_2CO_2R^1$, or
—$CH_2C(O) NR^1R^2$.

W and W' are each independently:
phenyl which is unsubstituted, mono- or polysubstituted by:
chlorine,
—$CF_3$,
fluorine,
—$NO_2$,
—$CO_2R^1$,
bromine,
—$SO_3H$,
—$SO_2NH_2$.

Also, W and W' are independently:

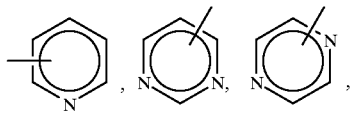

M and M' are each independently H, Me, or F.

More preferred compounds of the instant invention are those of Formula I wherein Z and Z' are each independently:
4-chlorophenyl,
4-(trifluoromethyl)phenyl,
4-nitrophenyl,
4-methylphenyl,
4-methoxyphenyl,
4-fluorophenyl,
4-cyanophenyl,
4-methylthiophenyl,
4-(methylsulfonyl)phenyl,
phenyl,
cyclohexyl, or
2-adamantyl;

A' is:

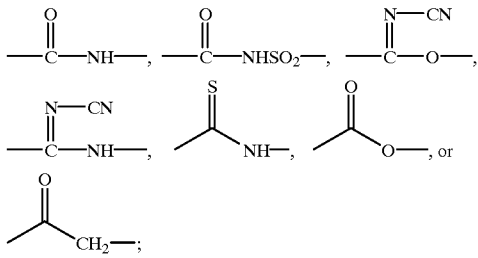

A is:

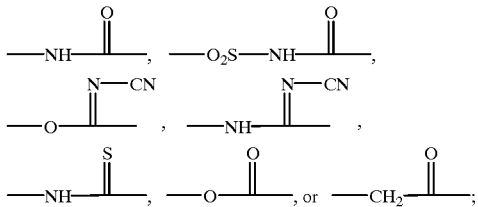

Q and Q' are each independently NY and NY' or oxygen;
Y and Y' are each independently hydrogen or methyl;
W and W' are each independently phenyl, -3-chlorophenyl or 2-chlorophenyl, and
M and M' are each H.

Still more preferred compounds of the instant invention are selected from
(+)-[S-(R*,R*)]-N-[[[1,2-diphenyl-2-[[[[4-(trifluoromethyl)phenyl]amino]carbonyl]amino]ethyl]amino]carbonyl]-4-methyl-benzenesulfonamide,

[S-(R*,R*)] and [R-(R*,R*)]-N-[1,2-diphenyl-2-[[[[4-(trifluoromethyl)phenyl]amino]carbonyl]amino]ethyl]-N'-(4-nitrophenyl)-urea, (+)-[S-(R*,R*)]-N-[[[2-[[[(4-chlorophenyl)-amino]carbonyl]amino)-1,2-diphenylethyl]amino]-carbonyl]-4-methyl-benzenesulfonamide

[S-(R*,R*)] and [R-(R*,R*)]-N-[[[2-[[[(4-chlorophenyl)amino]carbonyl]amino]-1,2-diphenylethyl]-amino]carbonyl]-benzenesulfonamide, and

[S-(R*,R*)] and [R-(R*,R*)I-4-methyl-N-[[[2-[[[(4-methylphenyl)amino]carbonyl]amino]-1,2-diphenylethyl]amino]carbonyl]-benzenesulfonamide.

Other compounds of the invention are:

[S-(R*,R*)] and [R-(R*,R*)]-N-(4-bromophenyl)-N'-[2-(formylamino)-1,2-diphenylethyl]-urea, Phenyl-[S-(R*,R*)] and [R-(R*,R*)]-N'-cyano-N-[1,2-diphenyl-2-[[[[4-(trifluoromethyl)phenyl]amino]carbonyl]amino]ethyl]-carbamate,

[R-(R*,R*)] and [S-(R*,R*)]-N-[2-(cyanoamino)-1,2-diphenylethyl]-N'-[4-(trifluoromethyl)phenyl]-urea,

[R-(R*,R*)] and [S-(R*,R*)]-N-[1,2-diphenyl-2-[[[(phenylmethyl)amino]thioxomethyl]amino]ethyl]-N'-[4-(trifluoromethyl)phenyl]-urea, Tricyclo[3.3.1.1$^{3.7}$]dec-2-yl[S-(R*,R*)] and [R-(R*,R*)]-[1,2-diphenyl-2-[[[[4-(trifluoromethyl) phenyl]amino]carbonyl]amino]ethyl]-carbamate,

[R-(R*,R*)] and [S-(R*,R*)]-N,N"-(1,2-diphenyl-1,2-ethanediyl)-bis[N'-[4-(trifluoromethyl)phenyl]-urea,

[S-(R*,R*)) and [R-(R*,R*)]-N-[1,2-diphenyl-2-[[[[4-(trifluoromethyl)phenyl]amino]carbonyl]amino]-ethyl]-benzamide,

[S-(R*,R*)] and [R-(R*,R*)]-N-[1,2-diphenyl-2-[[(phenylamino)thioxomethyl]amino]ethyl]-N'-[4-(trifluoromethyl)phenyl]-urea,

[S-(R*,R*)] and [R-(R*,R*)]-N-cyclohexyl-N'-[1,2-diphenyl-2-[[[[4-trifluoromethyl]phenyl]amino]carbonyl]amino]ethyl]-urea,

[R-(R*,R*)] and [S-(R*,R*)]-N-(3,4-dichlorophenyl)-N'-[1,2-diphenyl-2-[[[[4-(trifluoromethyl) phenyl]amino]carbonyl]amino]ethyl]-urea,

[R-(R*,R*)] and [S-(R*,R*)]-N-[1,2-diphenyl-2-[[[[4-(trifluoromethyl)phenyl)amino]carbonyl]-amino]ethyl]-N'-(4-methoxyphenyl)-urea,

[R-(R*,R*)] and [S-(R*,R*)]-N-[1,2-diphenyl-2-[[[[4-(trifluoromethyl)phenyl)amino]carbonyl]-amino]ethyl]-N'-(4-methylphenyl)-urea,

[S-(R*,R*)] and [R-(R*,R*)]-N-[1,2-diphenyl-2-[[[[4-trifluoromethyl)phenyl]amino]carbonyl]-amino]ethyl]-N-phenyl-urea,

[R-(R*,R*)] and [S-(R*,R*)]-N-(4-chlorophenyl)-N'-[1,2-diphenyl-2-[[[[4-(trifluoromethyl)phenyl]amino]carbonyl]amino]ethyl]-urea,

[R-(R*,R*)] and S-(R*,R*)]-N-[1,2-diphenyl-2-[[(tricyclo[3.3.1.1$^{3.7}$]dec-1-yl-amino)carbonyl]-amino]ethyl]-N'-[4-(trifluoromethyl)phenyl]-urea,

[R-(R*,R*)] and [S-(R*,R*)]-N-(2-amino-1,2-diphenylethyl)-N'-[4-(trifluoromethyl)phenyl]-urea,

[R-(R*,R*)] and [S-(R*,R*)]-N-[1,2-diphenyl-2-[[[[4-(trifluoromethyl)phenyl]amino]carbonyl]-amino]ethyl]-benzeneacetamide,

[R-(R*,R*)] and [S-(R*,R*)]-N-[1,2-diphenyl-2-[[[(3-methoxyphenyl)amino]carbonyl]amino[ethyl]-N'-[4-trifluoromethyl)phenyl]-urea,

[R-(R*,R*)] and [S-(R*,R*)]-N-[[[1,2-diphenyl-2-[[[[4-(trifluoromethyl)phenyl]amino]carbonyl]-amino]ethyl]amino]carbonyl]-4-methyl-benzene-sulfonamide,

[S-(R*,R*) and [R-(R*,R*)]-N-[1,2-diphenyl-2-[[[[4-(trifluoromethyl)phenyl]amino]carbonyl]-amino]ethyl]-cyclohexanecarboxamide,

[S-(R*,R*) and [R-(R*,R*)]-N-[1,2-diphenyl-2-[[[[4-trifluoromethyl)phenyl]amino]carbonyl]amino]-ethyl]-N'-(2-naphthalenyl)-urea,

[R-(R*,R*)] and [S-(R*,R*)]-N-(4-chlorophenyl)-N'-[2-[[(cyclohexylamino)carbonyl]amino]-1,2-diphenylethyl]-urea,

[R-(R*,R*)] and [S-(R*,R*)]-N-[2-[[(cyclohexylamino)carbonyl]amino]-1,2-diphenylethyl]-N'-(4-methoxyphenyl)-urea,

[R-(R*,R*)] and [S-(R*,R*)]-N,N'-(1,2-diphenyl-1,2-ethanediyl)bis[N'-cyclohexyl-urea, Methyl [R-(R*,R*)] and [S-(R*,R*)]-2-[[[[1,2-diphenyl-2-[[[[4-(trifluoromethyl)phenyl]-amino]carbonyl]amino]ethyl]amino]carbonyl]amino]-cyclohexanoate,

[R-(R*,R*)] and [S-(R*,R*)]-N-(2-chlorophenyl)-N'-[2-[[(cyclohexylamino)carbonyl]amino]-1,2-diphenyl-ethyl]-urea,

[R-(R*,R*)] and [S-(R*,R*)]-N-(3-chlorophenyl)-N'-[2-[[(cyclohexylamino)carbonyl]amino]-1,2-diphenyl-ethyl]-urea,

[R-(R*,R*)] and [S-(R*,R*)]-N-[2-[[(cyclohexyl-amino)carbonyl]amino]-1,2-diphenylethyl]-N'-(2-methoxyphenyl)-urea,

[R-(R*,R*)] and [S-(R*,R*)]-N-[1,2-diphenyl-2-[[[(2-methoxyphenyl)amino]carbonyl]amino]ethyl]-N'-[4-(trifluoromethyl)phenyl]-urea,

[R-(R*,R*)] and [S-(R*,R*)]-N-(3-chlorophenyl)-N'-[1,2-diphenyl-2-[[[[4-(trifluoromethyl)phenyl]amino]carbonyl]amino]ethyl]-urea,

[R-(R*,R*)] and [S-(R*,R*)]-N-(2-chlorophenyl)-N'-[1,2-diphenyl-2-[[[[4-(trifluoromethyl)phenyl]amino]carbonyl]amino]ethyl]-urea,

[R-(R*,R*)] and [S-(R*,R*)]-N-cyclohexyl-N'-[2-[[[(3-methoxyphenyl)amino]carbonyl]amino]-1,2-diphenylethyl]-urea 1,1-dimethylethyl [R-(R*,R*)] and [S-(R*,R*)]-[1,2-diphenyl-3-[[[[4-(trifluoromethyl)phenyl]amino]-carbonyl]amino]ethyl]-carbamate, Tricyclo[3.3.1.1$^{3.7}$]dec-2-yl-[R-(R*,R*)] and [S-(R*,R*)]-[2-[[(cyclohexylamino)carbonyl]amino]-1,2-diphenylethyl]-carbamate,

[S-(R*,R*)] and ER-(R*,R*)]-N-[[[2-[[[(4-chlorophenyl)amino]carbonyl]amino]-1,2-diphenylethyl]amino]-carbonyl]-4-methyl-benzenesulfonamide,

[R-(R*,R*)] and [S-(R*,R*)]-N-(4-chlorophenyl)-N'-[2-[[(1-naphthalenylamino)carbonyl]amino]-1,2-diphenylthyl]-urea,

[R-(R*,R*)] and [S-(R*,R*)]-N-[1,2-diphenyl-2-[[[[4-(trifluoromethyl)phenyl]amino]carbonyl]amino]-ethyl]-N'-(4-fluorophenyl)-urea,

[R-(R*,R*)] and [S-(R*,R*)]-N-(4-bromophenyl-N'-[1,2-diphenyl-2-[[[[4-(trifluoromethyl)phenyl]amino]-carbonyl]amino]ethyl]-urea, Tricyclo[3.3.1.1.$^{3.7}$]dec-2-yl-[R-(R*,R*)] and (S-(R*,R*)]-[2-[[[(4-chlorophenyl)amino]carbonyl]-amino]-1,2-diphenylethyl]-carbamate,

[R-(R*,R*)] and [S-(R*,R*)]-N-[2-[[[(4-chlorophenyl)amino]carbonyl]amino]-1,2-diphenylethyl]-1H-indole-3-acetamide,

[R-(R*,R*)] and [S-(R*,R*)]-N-[[[2-[[[[(4-nitrophenyl)amino]carbonyl]amino]-1,2-diphenylethyl]-amino]carbonyl]-4-methylbenzenesulfonamide,

[R-(R*,R*)] and [S-(R*,R*)]-N-[[[(4-chlorophenyl)-amino]carbonyl]amino]-1,2-diphenylethyl]-4-methylbenzenesulfonamide,

[S-(R*,R*)] and [R-(R*,R*)]-N-(4-chlorophenyl)-N'-[1,2-diphenyl-2-[[(phenylamino)carbonyl]amino]ethyl]-urea,

[S-(R*,R*)] and [R-(R*,R*)]-N-(4-nitrophenyl)-N'-[1,2-diphenyl-2-[[(phenylamino)carbonyl]amino]ethyl)-urea,

[S-(R*,R*)] and [R-(R*,R*)]-N-(4-chlorophenyl)-N'-[2-[[[(4-cyanophenyl)amino]thioxomethyl]amino]-1,2-diphenylethyl]-urea,

[R-(R*,R*)] and [S-(R*,R*)]-N-[[[2-[[[(3-chlorophenyl)amino]carbonyl]amino]-1,2-diphenylethyl]amino]-carbonyl]-4-methyl-benzenesulfonamide,

[R-(R*,R*)] and [S-(R*,R*)]-N-[[[2-[[[(4-methoxyphenyl)amino]carbonyl]amino]-1,2-diphenylethyl]amino]-carbonyl]-4-methyl-benzenesulfonamide,

[S-(R*,R*)] and [R-(R*,R*)]-N-[[[1,2-diphenyl-2-[[(phenylamino)carbonyl]amino]ethyl]amino]carbonyl]-4-methyl-benzenesulfonamide,

[S-(R*,R*)] and [R-(R*,R*)]-N-[[[2-[[[(2,4-difluorophenyl)amino]carbonyl]amino]-1,2-diphenylethyl]amino]carbonyl]-4-methylbenzenesulfonamide,

[S-(R*,R*)] and [R-(R*,R*)]-N-[[[2-[[(cyclohexylamino)carbonyl]amino]-1,2-diphenylethyl]amino]-carbonyl]-4-methyl-benzenesulfonamide,

[S-(R*,R*)]-N,N'-[[(1,2-diphenyl-1,2-ethanediyl)-amino]carbonyl]bis[4-methyl], benzenesulfonamide,

[R-(R*,R*)]-N,N'[[(1,²-diphenyl-1,2-ethanediyl)-amino]carbonyl]bis[⁴-methyl-benzenefulfonamide,

[S-(R*,R*)] and (R-(R*,R*)]-N-(4-chlorophenyl)-N'-[2-[[[[4-(methylthio)phenyl]amino)carbonyl]amino]1,2-diphenylethyl)-urea,

[S-(R*,R*)] and [R-(R*,R*)]-N-(4-chlorophenyl)-N'-[2-[[[[4-(methylsulfonyl)phenyl]amino]carbonyl]amino]-1,2-diphenylethyl]-urea,

[S-(R*,R*)] and [R-(R*,R*)]-N-cyclohexyl-N'-[2-[[[(4-nitrophenyl)amino]carbonyl]amino]-1,2-diphenylethyl]-urea,

[S-(R*,R*)] and [R-(R*,R*)]-N-cyclohexyl-N'-[2-[[[(4-cyanophenyl)amino]thioxomethyl]amino]-1,2-diphenylethyl]-urea,

[S-(R*,R*)] and (R-(R*,R*)]-N-[2-[[[4-cyanophenyl)amino]thioxomethyl]amino]-1,2-diphenylethyl]-N'-[4-(trifluoromethyl)phenyl]-urea,

[R-(R*,R*)] and [S-(R*,R*)]-N-[[(2-amino-1,2-diphenylethyl)-amino]carbonyl]-4-methylbenzenesulfonamide, (-)-[R-(R*,R*)]-N-(2-amino-1,2-diphenylethyl)-N'-(4-chlorophenyl)-urea, (+)-[S-(R*,R*)]-N-(²-amino-1,2-diphenylethyl)-N'-(4-chlorophenyl)-urea, (-)-[R-(R*,R*)]-N-(4-chlorophenyl)-N'-[1,2-diphenyl]-2-[[[[4-(trifluoromethyl)phenyl]amino]-carbonyl]amino]ethyl]-urea, (-)-[R-(R*,R*)]-N-[[[2-[[[(4-chlorophenyl)amino]-carbonyl]amino]-1,2-diphenylethyl]amino]carbonyl]-4-methylbenzenesulfonamide, and

[R-(R*,S*)]-N-(4-chlorophenyl)-N'-(2-hydroxy-1,2-diphenylethyl)-urea.

Ethyl-(-)-[S-(R*,R*))-3-[[[[2-[[[[(4-methylphenyl)sulfonyl]amino]carbonyl]amino]-1,2-diphenylethyl]amino]carbonyl]amino]benzoate.

(-)-[S-(R*,R*)]-3-[[[[-2-[[[[(4-methylphenyl)-sulfonyl]amino]carbonyl]amino]-1,2-diphenylethyl]-amino]carbonyl]amino]benzoic acid.

Ethyl-(-)-[S-(R*,R*)]-3-[[[[2-[[[(4-chlorophenyl)-amino]carbonyl]amino]-1,2-diphenylethyl]-amino]carbonyl]amino]benzoate.

(-)-[S-(R*,R*)]-3-[[[[2-[[((4-chlorophenyl)-amino]carbonyl]amino]-1,2-diphenylethyl]amino]-carbonyl]amino]benzoate.

The compounds of the invention include the solvates and hydrates and pharmaceutically acceptable salts of the compounds of Formula I.

The compounds of the present invention can have multiple chiral centers including those designated in the above Formula I by a *, depending on their structures. In addition, centers of asymmetry may exist on substituents Z and Z'. In particular the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by conventional methods well known in the art such as conversion to a salt with an optically active compound, followed by separation by recrystallization and reconversion to the nonsalt form or by chromatography using an optically active stationary phase.

The terms straight and branched alkyl meant to include carbon chains of from 1 to 6 carbon atoms except where specifically stated to be otherwise. Such terms include but are not limited to methyl, ethyl, n-propyl, isopropyl, n-butyl, sec-butyl, isobutyl, tert-butyl, n-pentyl, and n-hexyl.

The terms cyclo- and polycyclo alkyl include cyclic hydrocarbons with from 5 to 12 carbon atoms in one ring or in two fused rings. Such terms include, but are not limited to, adamantyl, cyclohexyl, and norbornyl.

The term polyaromatic includes, but is not limited to, naphthalyl and anthracyl.

The term heteroaromatic means and includes but is not limited to pyridyl, furan, pyrimidyl, pyridazine, and pyrazine.

The term hydroaromatic means and includes but is not limited to cyclohexene and cyclohexadiene.

The compounds of the present invention can be formed by sequential coupling of isocyanates, isothiocyanates, acid chlorides, chloroformates, cyanoimidates, sulfonyl chlorides, thioformates, alkylformates, and cyanogen bromide to the 1,2-disubstituted-1,2-ethylene diamine of Formula II.

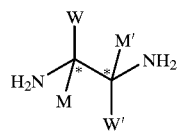

II

The compound wherein W and W' are both phenyl, and M and M' are H, and possess a (R*,R*) stereochemical relationship are commercially available in enantiomerically pure form (Fluka Chemical) or can be prepared in racemic form by the procedure of Corey E J, et al., *J Am Chem Soc* 1989;111:5493–5 and Supplementary Material. The racemic (R*,R*) Intermediate II can be resolved into its individual enantiomers by fractional recrystallization of its corresponding bis-tartaric acid salt (Williams O F, et al., *J Am Chem Soc* 1959;81:4464; and Saigo K, et al., *Bull Chem Soc Jpn* 1986;59:931)

Further, the (R*,S*) stereochemical isomer of the compound of Formula II, wherein W and W' are both phenyl and M and M' are hydrogen, can be prepared by the procedure of Williams O F, et al., *J Am Chem Soc* 1959;81:4464 or by the procedure of Schönenberger H, et al., *J Med Chem* 1990;33:2535.

The (R*,R*) and (R*,S*) stereochemical isomers of Formula II, wherein W and WI are substituted phenyl, and M and M' are hydrogens, can be prepared by the method of Schönenberger H, et al., *J Med Chem* 1990;33:2535, from E- and Z-stilbenes, respectively.

The desired compounds of Formula I are prepared by reaction of compounds of Formula II with one molar equivalent of a reactive acylating type agent (e.g., an isocyanate) to give compounds of Formula III, a subset of Formula I

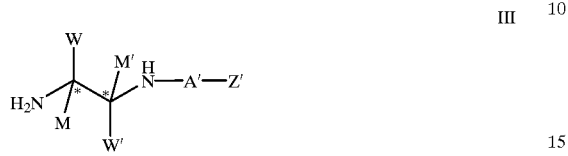

III where W, W', A', M, M', and Z' are described above. The procedures and purification routines required to give the mono acylated adducts are described fully in the experimental section below.

Compounds of Formula III are then subjected to treatment with a second active acylating agent; as described previously; to give desired compounds of Formula I.

Scheme I below illustrates procedures for preparing intermediates useful in producing products of Formula II.

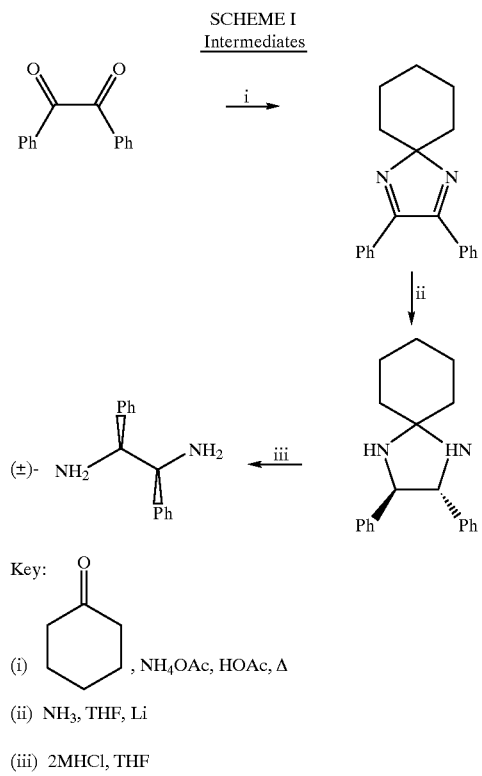

Key:
(i) <cyclohexanone>, NH₄OAc, HOAc, Δ

(ii) NH₃, THF, Li (iii) 2M HCl, THF

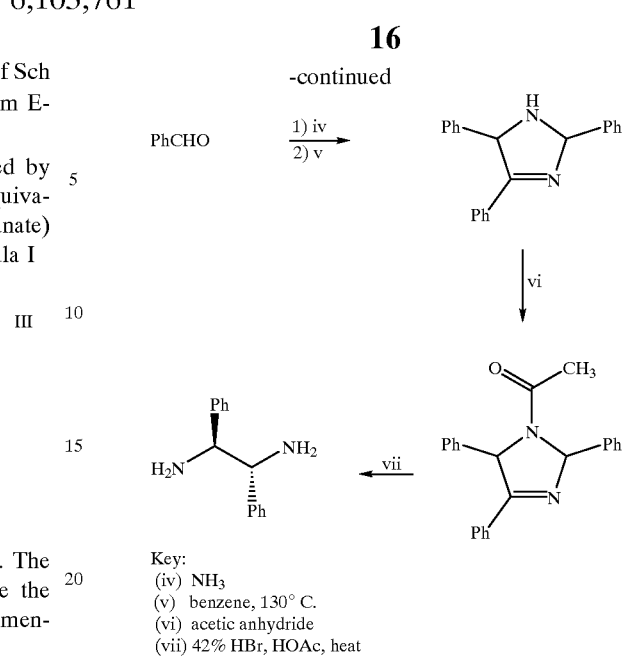

Key:
(iv) NH₃
(v) benzene, 130° C.
(vi) acetic anhydride
(vii) 42% HBr, HOAc, heat

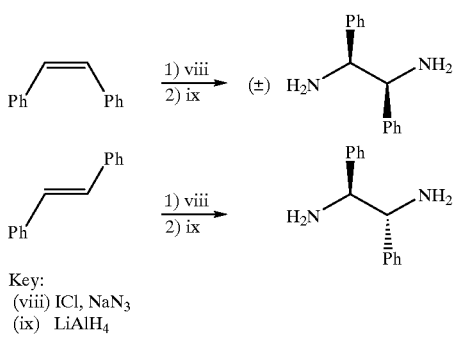

Key:
(viii) ICl, NaN₃
(ix) LiAlH₄

Scheme II illustrates how compounds of Formula III are produced from the reaction of compounds of Formula II with reactive acyl-type reagents. The reaction conditions used allow for the simple filtration isolation of the mono-adducts or by stopping the reaction at a set point and separating the statistical mixture of unreacted II, desired mono-adducts III, and the bis-adducts by chromatography.

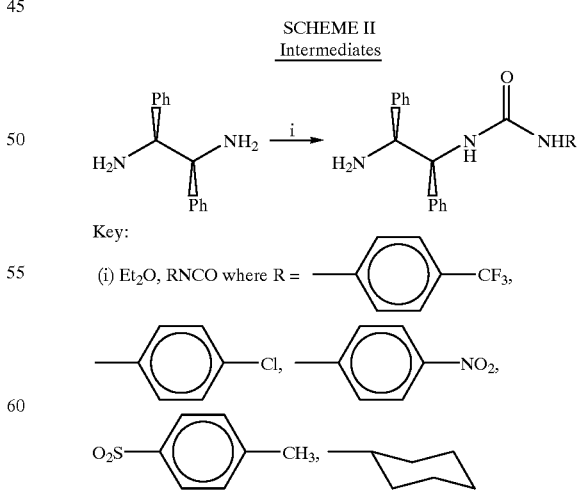

Key:
(i) Et₂O, RNCO where R =

The desired compounds of Formula I are prepared by reacting an appropriate intermediate of Formula III with one molar equivalent of a reactive acylating agent Scheme III.
Biological Activity
The biological activity of compounds of the present invention was evaluated employing an initial screening test
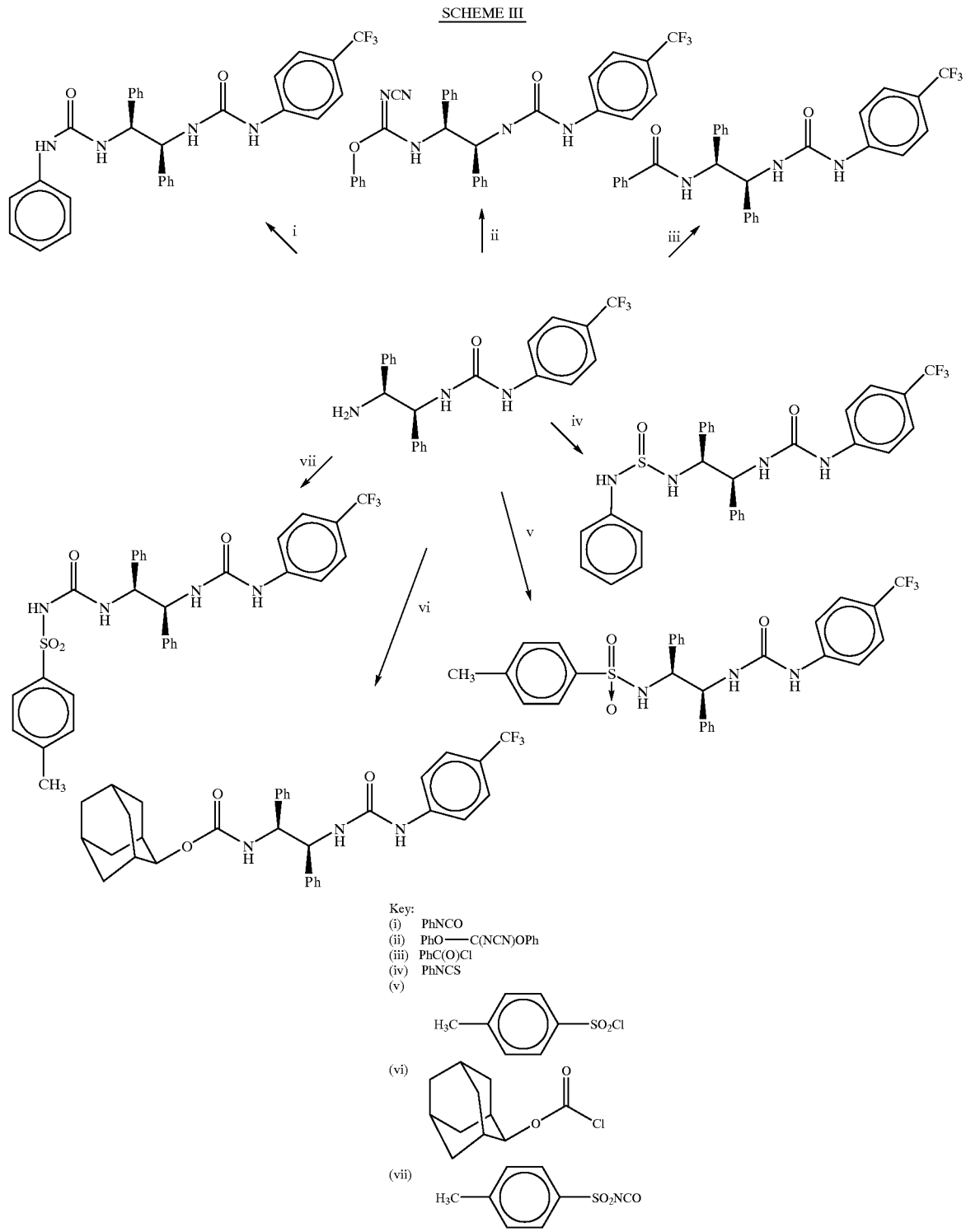

which rapidly and accurately measured the binding of the tested compound to known CCK receptor sites. Specific CCK receptors have been shown to exist in the central nervous system. (See Hays, et al., *Neuropeptides* 1980;1:53–62; and Satuer, et al., *Science* 1980;208:1155–6.)

In this screening test, the cerebral cortices taken from male CFLP mice weighing between 30–40 g were dissected on ice, weighed, and homogenized in 10 volumes of 50 mM Tris-HCl buffer (pH 7.4 at 0–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM $MgCl_2$, 1 nM EDTA, 5 mg/mL bovine albumin, and bacitracin (0.25 mg/mL).

In saturation studies, cerebral cortical membranes were incubated at 23° C. for 120 minutes in a final volume of 500 μL of Hepes incubation buffer (pH 7.2) together with 0.2–20 nM tritiated-pentagastrin (Amersham International, England).

In the displacement experiments, membranes were incubated with a single concentration (2 nM) of ligand, together with increasing concentrations ($10^{-11}$ to $10^{-14}$M) of competitive test compound. In each case, the nonspecific binding was defined as that persisting in the presence of the unlabeled octapeptide $CCK_{26-33}$ ($10^{-6}$M).

Following incubation, radioactivity bound to membranes was separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47%–52%).

The specific binding to CCK receptor sites was defined as the total bound tritiated-pentagastrin minus the amount of tritiated-pentagastrin bound in the presence of $10^{-6}$ octapeptide, $CCK_{26-33}$.

Saturation curves for specific tritiated-pentagastrin binding to mouse cortical membranes were analyzed by the methods of Scatchard (*Ann New York Acad Sci* 1949;51:660–72, and Hill, *J Physiol* 1910;40:IV–VIII), to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson, Redbard, 1978) to provide estimates of the $IC_{50}$ and nH (apparent Hill coefficient) values). ($IC_{50}$ values were defined as the concentration of test compound required to produce 50% inhibition of specific binding.)

The inhibition constant ($K_i$) of the test compound was then calculated according to the Cheng-Prusoff equation:

$$K_i = \frac{IC_{50}}{1 + [L]/K_a}$$

where [L] is the concentration of radiolabel and $K_a$ is the equilibrium dissociation constant.

The $K_i$ values for several representative compounds of the present invention are present in Table I below.

TABLE I

| Example Number | Binding Affinity CCK-B (nM) |
|---|---|
| 10 | 371 |
| 14 | 188 |
| 15 | 309 |
| 46 | 188 |
| 47 | 290 |
| 54 | 178 |
| 64 | 93 |
| 65 | 293 |

As can be seen in Table I above, the compounds of the instant invention have good binding affinity for the CCK-B receptor and are thus expected to be useful in treating anxiety, gastric acid secretion, appetite problems, gastrointestinal ulcers, psychosis (especially schizophrenia) and the withdrawal response produced by the above treatment or abuse of drugs or alcohol.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5% to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable counterions are shown below:

Acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoata (embonate), pantothenate, phosphate/diphosphate, polygalacturonate, salicylate, stearate, subacetate, succinate, sulfate, tannate, tartrate, teoclate, triethiodide, benzathine, chloroprocaine, choline, diethanolamine, ethylenediamine, meglumine, procaine, aluminum, calcium, lithium, magnesium, potassium, sodium, and zinc.

A preferred pharmaceutically acceptable salt is the N-methyl glucamine salt or sodium salt.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following examples are illustrative of the compounds of the instant invention. They are not intended to limit the scope of the invention.

EXAMPLE 1

Procedure A:

To a solution of [R-(R*,R*)] and [S-(R*,R*)]-1,2-diamino-1,2-diphenylethane (2.0 g, 9.4 mmol) in diethyl ether (20 mL) is added dropwise a solution of the appropriate isocyanate (9.4 mmol) in diethyl ether (10 mL). The desired mono-urea begins to precipitate shortly after addition begins. After the addition is complete, the mixture is stirred 0.5 hour before the product is filtered and washed with diethyl ether (3×20 mL). Dry in vacuo at 114° C.

[R-(R*,R*)] and [S-(R*,R*)]-N-(2-amino-1,2-diphenylethyl)-N'-[4-(trifluoromethyl)phenyl]urea

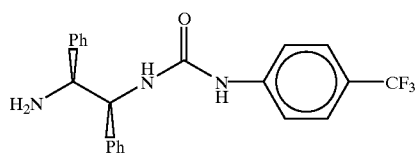

Using Procedure A: Reaction with 4-trifluoromethylphenyl isocyanate gives 42% of desired white solid, mp 223–227° C.

IR (KBr): 3025–3370, 1657, 1604, 1548, 1324, 1115;

NMR (DMSO-$d_6$): 1.7 (bs, 2H), 4.2 (d, 1H, J=4.1 Hz), 4.8 (dd, 1H, J=4.1, 10.1 Hz), 7.1–7.5 (m, 15H), 9.2 (s, 1H).

Analysis calculated for $C_{22}H_{20}F_3N_3O$: C, 66.16; H, 5.05; N, 10.52. Found: C, 66.36; H, 5.07; N, 10.39.

EXAMPLE 2

[R-(R*,R*)] and (S-(R*,R*)]-N-[[(2-amino-1,2-diphenylethyl)amino]carbonyl]-4-methyl-benzenesulfonamide

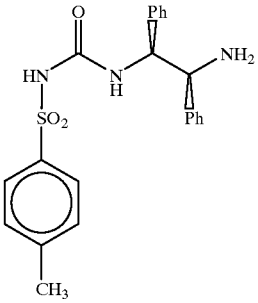

Using Procedure A: Reaction with p-toluenesulfonyl isocyanate gives 74% of desired white solid, mp 183–184° C.

IR (KBr): 3300–2345, 1690, 1585, 1495, 1231, 1125, 1084;

NMR (DMSO-$d_6$, TFA): 2.4 (bs, 3H), 4.6–5.0 (m, 2H), 6.9–7.4 (m, 14H), 7.8 (m, 2H), 8.6 (bm, 1H).

Analysis calculated for $C_{22}H_{23}N_3O_3S.0.2H_2O$: C, 63.96; H, 5.71; N, 10.17. Found: C, 64.05; H, 5.77; N, 10.07.

EXAMPLE 3

[R-(R*,R*)] and [S-(R*,R*)]-N-(2-amino-1,2-diphenylethyl)-N'-(4-nitrophenyl)urea

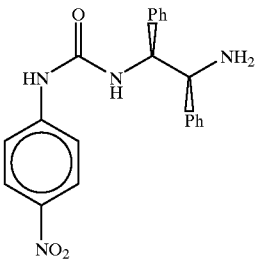

Using Procedure A: Reaction with 4-nitrophenyl isocyanate gives 20% of desired pale-yellow solid, mp 224–228° C.

IR (KBr): 3367, 1669, 1554, 1505, 1330, 700 cm$^{-1}$.

Analysis calculated for $C_{21}H_{20}N_4O_3$: C, 67.01; H, 5.36; N, 14.88. Found: C, 66.94; H, 5.44; N, 14.88.

EXAMPLE 4

Procedure B:

To a solution of [S-(R*,R*)] and [R-(R*,R*)]-1,2-diamino-1,2-diphenylethane (0.96 g, 4.5 mmol) in diethyl ether (10 mL) is added dropwise a solution of the isocyanate (4.5 mmol) in diethyl ether (10 mL). The reaction was closely monitored by TLC (18:1:1, EtOAc/H$_2$O/HCO$_2$H). After ¾ of the solution is added, the amount of desired product appears to be at maximum. The addition is stopped and the mixture is concentrated in vacuo. The mixture is purified by flash chromatography (SiO$_2$, 1:1 EtOAc/Hexane eluent). Concentration followed by crystallization from diethyl ether provides the desired products.

[S-(R*,R*)] and [R-(R*,R*)]-N-(2-amino-1,2-diphenylethyl)-N'-cyclohexylurea

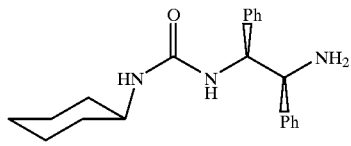

Using Procedure B: Reaction with cyclohexyl isocyanate gives (21%) of desired white solid, mp 136–137° C.

NMR (DMSO-$d_6$): 0.9–1.8 (m, 10H), 2.1 (br s, 1H), 3.1–3.5 (br s, 2H), 4.2 (m, 1H), 4.8 (m, 1H), 6.1 (d, 1H, J=7.7 Hz), 6.5 (d, 1H, J=7.7 Hz), 7.3 (m, 10H).

EXAMPLE 5
(+)-[S-(R*,R*)]-N-(2-amino-1,2-diphenylethyl)-N'-(4-chlorophenyl)urea

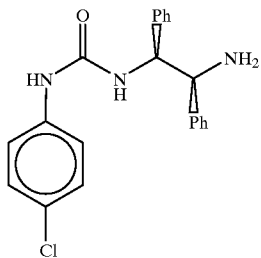

Using Procedure B: Reaction with 4-chlorophenyl isocyanate and (−)-[S-(R*,R*)]-1,2-diamino-1,2-diphenylethane gives (29%) of desired white solid, mp 174–175° C.

IR (KBr): 3328, 1649, 1548, 1491, 1231, 700;

NMR (DMSO-$d_6$): 1.7 (br s, 2H), 4.2 (d, 1H, J=4.1 Hz), 4.8 (dd, 1H, J=4.1, 8.0 Hz), 6.9 (d, 1H, J=8.0 Hz), 7.1–7.4 (m, 14H), 8.9 (s, 1H).

Analysis calculated for $C_{21}H_{20}ClN_3O$: C, 68.94; H, 5.51; N, 11.49. Found: C, 68.63; H, 5.35; N, 11.20.

$[\alpha]_D^{25}$=+26.1 (c=1, MeOH)

EXAMPLE 6
(−)-[R-(R*,R*)]-N-(2-amino-1,2-diphenylethyl)-N'-(4-chlorophenyl)urea

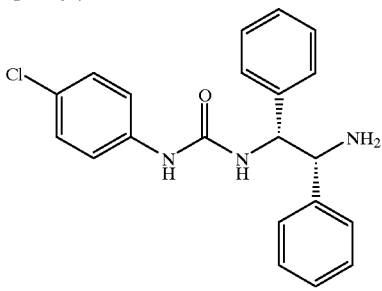

Using Procedure B: Reaction with 4-chlorophenyl isocyanate and (+)-[R-(R*,R*)]-1,2-diamino-1,2-diphenylethane gives (40%) of desired white solid, mp 173–174° C.

IR (KBr): 3328, 1649, 1548, 1491, 1231, 700;

NMR (DMSO-$d_6$): 1.7 (br 8, 2H), 4.2 (d, 1H, J=4.1 Hz), 4.8 (dd, 1H, J=4.1, 8.0 Hz), 6.9 (d, 1H, J=8.0 Hz), 7.1–7.4 (m, 14H), 8.9 (s, 1H).

Analysis calculated for $C_{21}H_{20}ClN_3O$: C, 68.94; H, 5.51; N, 11.49. Found: C, 68.81; H, 5.42; N, 11.41.

$[\alpha]_D^{25}$=−26.8 (c=1, MeOH)

EXAMPLE 7
Ethyl-(+)-[S-(R*,R*)]-3-[[[(2-amino-1,2-diphenylethyl)-amino]carbonyl]amino]benzoic acid

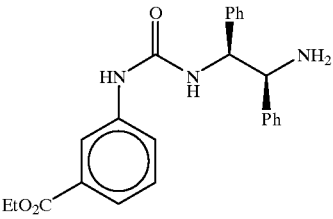

Using Procedure B: Reaction with ethyl 3-isocyanatobenzoate and (−)-[S-(R*,R*)]-1,2-diamino-1,2-diphenylethane gives 29% of desired white solid, mp 154–155.5° C.

IR (KBr): 3325, 1718, 1650, 1554, 1238, 700 cm$^{-1}$.

NMR (DMSO-$d_6$): δ 1.36 (t, 3H, J=7.1 Hz), 1.97 (br s, 2H), 4.31 (m, 3H), 5.06 (m, 1H), 6.69 (d, 1H, J=7.6 Hz), 7.27 (m, 10H), 7.47 (d, 1H, J=7.8 Hz), 7.67 (d, 1H, J=7.6 Hz), 7.88 (m, 2H).

Analysis calculated for $C_{24}H_{25}N_3O_3$: C, 71.44; H, 6.25; N, 10.41. Found: C, 71.41; H, 6.27; N, 10.38.

$[\alpha]_D^{25}$=+21.5° C. (c=1, MeOH).

EXAMPLE 8

Procedure C:

To a solution of [S-(R*,R*)] and [R-(R*,R*)]-N-(2-amino)-1,2-diphenylethyl)-N'-[4-(trifluoromethyl)-phenyl]urea (0.2 g, 0.5 mmol) in diethyl ether (10 mL) is added the isocyanate (0.5 mmol) or isothiocyanate in one portion. The resulting mixture is stirred 1 hour at room temperature before filtering off the solid product. The product is suspended in hot diethyl ether, filtered, and dried in vacuo at 114° C. for 4 hours.

[S-(R*,R*)] and [R-(R*,R*)]-N-cyclohexyl-N'-[1,2-diphenyl-2-[[[[4-trifluoromethyl)phenyl]amino]-carbonyl]amino]ethyl]urea

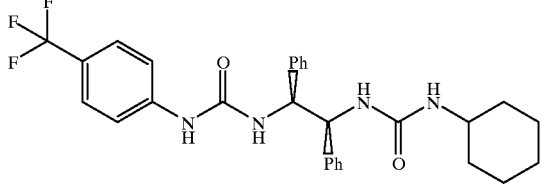

Using Procedure C: Reaction with cyclohexyl isocyanate gives 60% of desired white solid, mp 224° C.

NMR (DMSO-$d_6$): 0.95–1.24 (m, 5H), 1.49–1.62 (m, 5H), 4.95 (t, 2H, J=9.8 Hz), 5.93 (d, 1H, J=7.9), 6.41 (d, 1H, J=7.9 Hz), 6.9–7.22 (m, 11H), 7.55 (m, 4H), 9.15 (s, 1H).

Analysis calculated for $C_{29}H_{31}F_3N_4O_2$: C, 66.40; H, 5.96; N, 10.68. Found: C, 66.16; H, 5.82; N, 10.47.

EXAMPLE 9

[S-(R*,R*)] and [R-(R*,R*)]-N-[1,2-diphenyl-2-[[[[4-trifluoromethyl)phenyl]amino]carbonyl]-amino]ethyl]-N-phenyl]urea

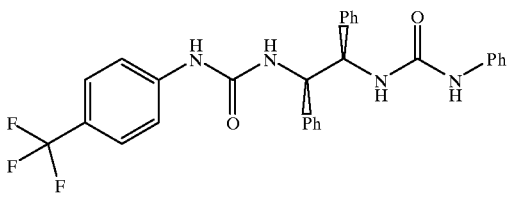

Using Procedure C: Reaction with phenylisocyanate gives 52% of desired white solid, mp 239–244° C.

NMR (DMSO-$d_6$): 5.1 (m, 2H), 6.8–7.6 (m, 21H), 8.6 (s, 1H), 9.0 (s, 1H).

Analysis calculated for $C_{29}H_{25}F_3N_4O_2$: C, 67.17; H, 4.86; N, 10.80. Found: C, 67.42; H, 4.95; N, 10.78.

EXAMPLE 10

[R-(R*,R*)] and [S-(R*,R*)]-N-(4-chlorophenyl)-N'-[1,2-diphenyl-2-[[[[4-(trifluoromethyl)phenyl]amino]-carbonyl]amino]ethyl]-urea

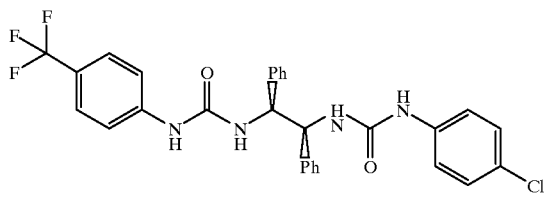

Using Procedure C: Reaction with 4-chlorophenyl isocyanate gives 51% of desired white solid, mp 272–274° C.

NMR (DMSO-$d_6$): 5.05 (m, 2H), 6.8–7.7 (m, 20H), 8.6 (s, 1H), 9.1 (s, 1H).

Analysis calculated for $C_{29}H_{24}N_4ClF_3O_2 \cdot 0.42H_2O$: C, 62.14; H, 4.27; N, 9.99. Found: C, 62.13; H, 4.25; N, 9.68.

EXAMPLE 11

[R-(R*,R*)] and [S-(R*,R*)]-N-(3,4-dichlorophenyl)-N'-[1,2-diphenyl-2-[[[[4-(trifluoromethyl)phenyl]amino]-carbonyl]amino]ethyl]urea

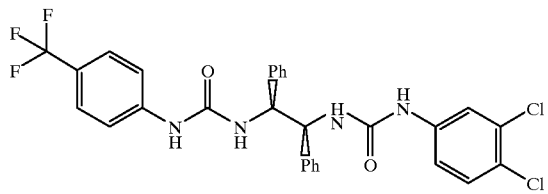

Using Procedure C: Reaction with 3,4-dichlorophenyl isocyanate gives 48% of desired white solid, mp 269–270° C.

NMR (DMSO-$d_6$): 5.0 (m, 2H), 7.0–7.6 (m, 18H), 7.8 (s, 1H), 8.9 (s, 1H), 9.0 (s, 1H).

Analysis calculated for $C_{29}H_{23}Cl_2F_3N_4O_2$: C, 59.30; H, 3.95; N, 9.54. Found: C, 59.09; H, 3.81; N, 9.35.

EXAMPLE 12

[R-(R*,R*)] and [S-(R*,R*)]-N-[1,2-diphenyl-2-[[[[4-(trifluoromethyl)phenyl]amino]carbonyl]amino]-ethyl]-N'-(4-methoxyphenyl)urea

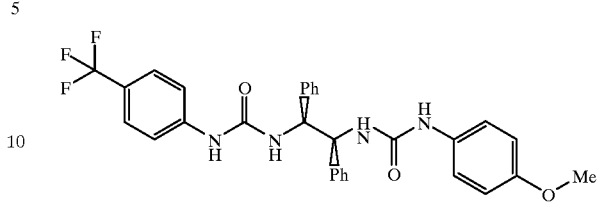

Using Procedure C: Reaction with 4-methoxyphenyl isocyanate gives 80% of desired white solid, mp 260–261° C.

IR (KBr): 3000–3600 br, 1653, 1605, 1564, 1553, 1512, 1326 cm$^{-1}$;

NMR (DMSO): 3.67 (s, 3H), 5.0 (m, 2H), 6.77 (d, 3H, J=8.9 Hz), 7.02–7.31 (m, 13H), 7.56 (m, 4H), 8.41 (s, 1H), 9.09 (s, 1H).

Analysis calculated for $C_{30}H_{27}F_3N_4O_3$: C, 65.69; H, 4.96; N, 10.21. Found: C, 65.50; H, 4.79; N, 10.14.

EXAMPLE 13

[R-(R*,R*)] and [S-(R*,R*)]-N-[1,2-diphenyl-2-[[[[4-(trifluoromethyl)phenyl]amino]carbonyl]amino]-ethyl]-N'-(4-methylphenyl)urea

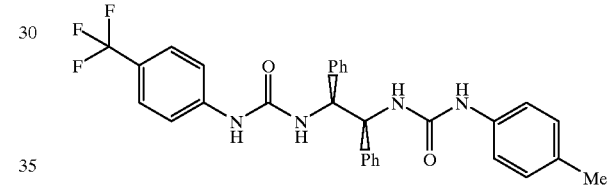

Using Procedure C: Reaction with 4-methylphenyl isocyanate gives 95% of desired white solid, mp 232–243° C.

NMR (DMSO-$d_6$): 2.19 (s, 3H), 5.02 (m, 2H), 6.86–7.60 (m, 23H), 8.53 (s, 1H), 9.13 (s, 1H).

Analysis calculated for $C_{30}H_{27}F_3N_4O_2 \cdot 0.5H_2O$: C, 66.53; H, 5.21; N, 10.35. Found: C, 66.34; H, 5.00; N, 10.12.

EXAMPLE 14

[S-(R*,R*)] and [R-(R*,R*)]-N-[[[1,2-diphenyl-2-[[[[4-(trifluoromethyl)phenyl]amino]carbonyl]amino]-ethyl]amino]carbonyl]-4-methyl-benzenesulfonamide

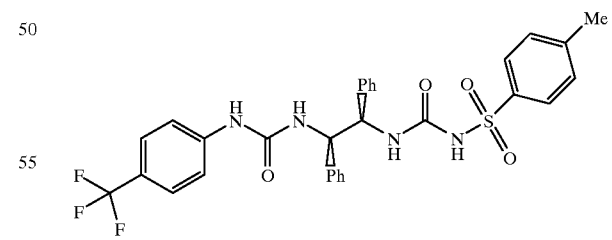

Using Procedure C: Reaction with 4-methylbenzenesulfonyl isocyanate gives 72% of desired white solid, mp 210–212° C.

NMR (DMSO-$d_6$): 2.31 (s, 3H), 4.87 (t, 1H, J=8.0 Hz), 5.00 (t, 1H, J=8.0 Hz), 6.9–7.26 (m, 13H), 7.27 (2H, J=8.0 Hz) 7.59 (s, 4H), 7.70 (d, 2H), 8.97 (s, 1H).

Analysis calculated for $C_{30}H_{27}N_4F_3O_4S$: C, 60.19; H, 4.88; N, 9.36. Found: C, 60.07; H, 4.50; N, 9.16.

EXAMPLE 15
[S-(R*,R*)] and [R-(R*,R*)]-N-[1,2-diphenyl-2-[[[[4-(trifluoromethyl)phenyl]amino]carbonyl]amino]-ethyl]-N'-(4-nitrophenyl)urea

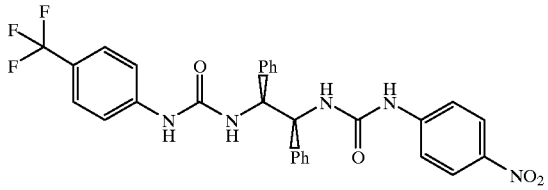

Using Procedure C: Reaction with 4-nitrophenyl isocyanate gives 36% of desired yellow solid, mp 268–269° C.

IR (KBr): 3250, 1670, 1610, 1580, 1520, 1335, 1115 cm$^{-1}$;

NMR (DMSO-d$_6$): 5.05 (m, 2H), 7.10–7.61 (m, 15H), 7.73 (d, 1H, J=9.2 Hz), 8.09 (d, 2H, J=9.2 Hz), 8.22 (d, 1H, J=9.2 Hz), 9.06 (s, 1H), 9.43 (s, 1H), 9.76 (s, 1H).

Analysis calculated for C$_{29}$H$_{24}$F$_3$N$_5$O$_4$:

EXAMPLE 16
[S-(R*,R*)] and [R-(R*,R*)]-N-[1,2-diphenyl-2-[[[(3-methoxyphenyl)amino]carbonyl]amino]ethyl]-N'-[4-trifluoromethyl)phenyl]urea

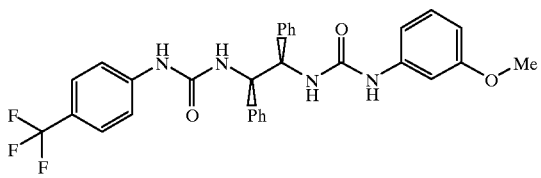

Using Procedure C: Reaction with 3-methoxyphenyl isocyanate gives 72% of desired white solid, mp 213–216° C.

NMR (DMSO-d$_6$): 3.67 (s, 3H), 5.01 (m, 2H), 6.44 (dd, 1H, J=2.2, 8.8 Hz), 6.84 (dd, 1H, J=2.2, 8.8 Hz), 7.04–7.23 (m, 17H), 7.55–7.60 (m, 4H), 8.64 (s, 1H), 9.09 (s, 1H).

Analysis calculated for C$_{30}$H$_{27}$F$_3$N$_4$O$_3$: C, 65.69; H, 4.96; N, 10.21. Found: C, 65.30; H, 5.03; N, 10.06.

EXAMPLE 17
[S-(R*,R*)] and [R-(R*,R*)]-N-[1,2-diphenyl-2-[[[[4-trifluoromethyl)phenyl]amino]carbonyl]amino]-ethyl]-N'-(2-naphthalenyl)urea

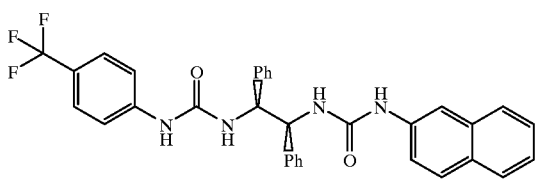

Using Procedure C: Reaction with 2-napthyl isocyanate gives 48% of desired white solid, mp 245–246° C.

IR (KBr): 3400 br, 1660, 1570, 1430, 1075 cm$^{-1}$;

NMR (DMSO-d$_6$): 5.09 (m, 2H), 7.06–8.03 (m, 23H), 8.70 (s, 1H), 9.09 (s, 1H).

Analysis calculated for C$_{33}$H$_{27}$F$_3$N$_4$O$_2$: C, 69.71; H, 4.79; N, 9.85. Found: C, 69.54; H, 4.59; N, 9.80.

EXAMPLE 18
[R-(R*,R*)] and [S-(R*,R*)]-N-[1,2-diphenyl-2-[[[(2-methoxyphenyl)amino]carbonyl]amino]ethyl]-N'-[4-(trifluoromethyl-)phenyl]urea

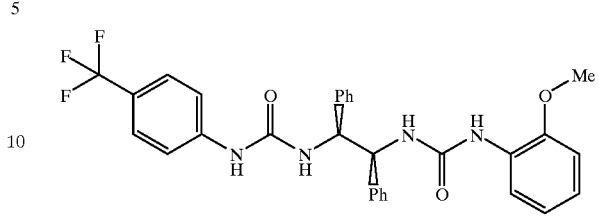

Using Procedure C: Reaction with 2-methoxyphenyl isocyanate gives 64% of desired white solid, mp 250–251° C.

IR (KBr): 3340, 1654, 1550, 1326, 1114, 700 cm$^{-1}$;

NMR (DMSO-d$_6$): 3.79 (s, 3H), 5.03 (m, 2H), 7.03–7.23 (m, 13H), 7.54 (m, 4H), 7.65 (d, 2H, J=7.6 Hz), 8.08–8.13 (m, 2H), 9.08 (s, 1H).

Analysis calculated for C$_{30}$H$_{27}$F$_3$N$_4$O$_3$: C, 65.69; H, 4.96; N, 10.21. Found: C, 65.55; H, 5.02; N, 10.00.

EXAMPLE 19
[R-(R*,R*)] and [S-(R*,R*)]-N-(2-chlorophenyl)-N'-[1,2-diphenyl-2-[[[[4-(trifluoromethyl)phenyl]amino]-carbonyl]amino]ethyl]urea

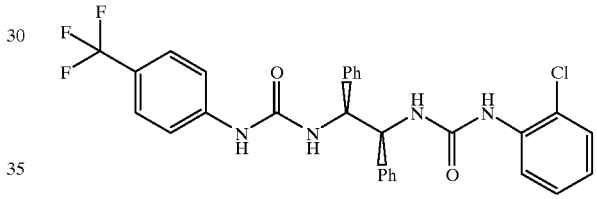

Using Procedure C: Reaction with 2-chlorophenyl isocyanate gives 52% of desired white product, mp 244–246° C.

IR (KBr): 3340, 1658, 1552, 1326, 1116, 699 cm$^{-1}$;

NMR (DMSO-d$_6$): 5.02 (m, 2H), 6.89–7.38 (m, 14H), 7.54 (m, 4H), 7.78 (m, 1H), 8.13 (dd, 1H, J=1.0 Hz, 8.5 Hz), 8.23 (s, 1H), 9.09 (s, 1H).

Analysis calculated for C$_{29}$H$_{24}$ClF$_3$N$_4$O$_2$·0.29H$_2$O: C, 62.40; H, 4.44; N, 10.04. Found: C, 62.43; H, 4.21; N, 9.88.

EXAMPLE 20
[R-(R*,R*)] and [S-(R*,R*)]-N-(3-chlorophenyl)-N'-[1,2-diphenyl-2-[[[[4-(trifluoromethyl)phenyl]amino]-carbonyl]amino]ethyl]urea

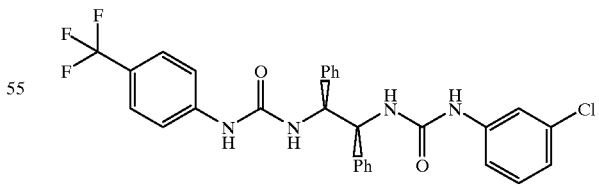

Using Procedure C: Reaction with 3-chlorophenyl isocyanate gives 64% of desired white solid, mp 246° C.–247° C.

IR (KBr): 3338, 1656, 1594, 1553, 1326, 699 cm$^{-1}$;

NMR (DMSO-d$_6$): 5.03 (m, 2H), 7.02–7.24 (m, 15H), 7.51–7.69, (m, 5H), 8.34 (s, 1H), 9.07 (s, 1H).

Analysis calculated for C$_{29}$H$_{24}$ClF$_3$N$_4$O$_2$: C, 62.99; H, 4.37; N, 10.13. Found: C, 62.94; H, 4.20; N, 9.99.

EXAMPLE 21
[R-(R*,R*)] and [S-(R*,R*)]-N-[1,2-diphenyl-2-[[[[4-(trifluoromethyl)phenyl]amino]carbonyl]amino]-ethyl]-N'-(4-fluorophenyl)urea

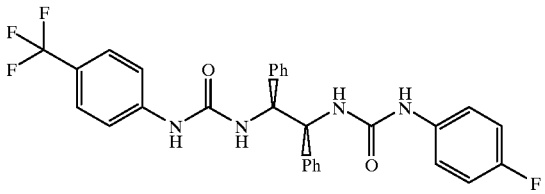

Using Procedure C: Reaction with 4-fluorophenyl isocyanate gives 52% of desired white solid, mp 254–256° C.
IR (KBr): 3331, 1653, 1558, 1509, 1326, 699 cm$^{-1}$;
NMR (DMSO-d$_6$): 5.02 (m, 2H), 6.86–7.59 (m, 20H), 8.64 (s, 1H), 9.07 (s, 1H).
Analysis calculated for C$_{29}$H$_{24}$F$_4$N$_4$O$_2$.0.5H$_2$O: C, 63.85; H, 4.62; N, 10.27. Found: C, 64.07; H, 4.38; N, 10.20.

EXAMPLE 22
[R-(R*,R*)] and [S-(R*,R*)]-N-(4-bromophenyl)-N'-[1,2-diphenyl-2-[[[[4-(trifluoromethyl)phenyl]amino]-carbonyl]amino]ethyl]urea

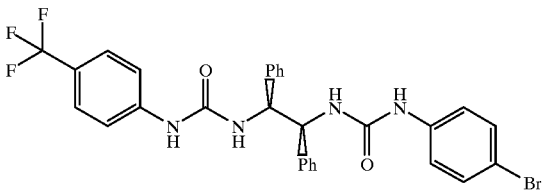

Using Procedure C: Reaction with 4-bromophenyl isocyanate gives 48% of desired product, mp 281–282.5° C.
IR (KBr): 3330, 1654, 1559, 1547, 1324, 698 cm$^{-1}$;
NMR (DMSO-d$_6$): 5.03 (s, 2H), 6.93–7.62 (m, 20H), 8.78 (s, 1H), 9.07 (s, 1H).
Analysis calculated for C$_{29}$H$_{24}$BrF$_3$N$_4$O$_2$: C, 58.30; H, 4.05; N, 9.38. Found: C, 58.48; H, 4.15; N, 9.25.

EXAMPLE 23
[S-(R*,R*)] and [R-(R*,R*)]-N-[2-[[[4-cyanophenyl)-amino]thioxomethyl]amino]-1,2-diphenylethyl]-N'-[4-(trifluoromethyl)phenyl]urea

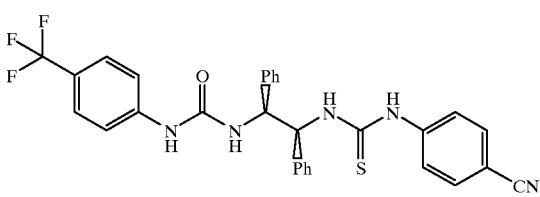

Using Procedure C: Reaction with 4-cyanophenyl isothiocyanate gives 39* of desired product, mp 169–172° C.
IR (KBr): 3340, 2228, 1605, 1541, 1326, 700 cm$^{-1}$;
NMR (DMSO-d$_6$): 5.17 (t, 1H, J=9.7 Hz), 5.78 (t, 1H, J=9.7 Hz), 7.13–7.74 (m, 19H), 8.9 (d, 1H, J=9.7 Hz), 9.08 (s, 1H), 10.20 (s, 1H).
Analysis calculated for C$_{30}$H$_{24}$F$_3$N$_5$OS.0.5H$_2$O: C, 63.25; H, 4.44; N, 12.19. Found: C, 63.63; H, 4.46; N, 11.86.

EXAMPLE 24
[R-(R*,R*)] and [S-(R*,R*)]-N-[1,2-diphenyl-2-[[[(phenylmethyl)amino]thioxomethyl]amino]ethyl]-N'-[4-(trifluoromethyl)phenyl]urea

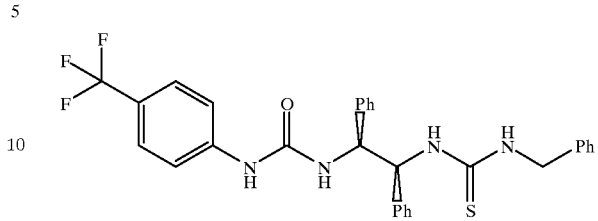

Using Procedure C: Reaction with benzyl isothiocyanate gives 15% desired product, mp 195–196° C.
IR (KBr): 3200–3450, 1554, 1326, 1115, 698 cm$^{-}$;
NMR (DMSO-d$_6$): 4.53 (m, 1H), 4.74 (br s, 1H), 5.13 (8, 1H), 5.82 (br s, 1H), 7.08–7.57 (m, 20H), 7.97–8.19 (m, 2H), 9.14 (br s, 1H).
Analysis calculated for C$_{30}$H$_{27}$F$_3$N$_4$OS: C, 65.68; H, 4.96; N, 10.21. Found: C, 65.96; H, 5.18; N, 9.97.

EXAMPLE 25
[R-(R*,R*)] and [S-(R*,R*)]-N,N'-(1,2-diphenyl-1,2-ethanediyl)bis[N'-[4-(trifluoromethyl)phenyl]urea

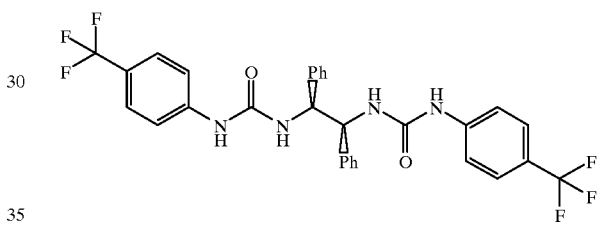

Using Procedure C: Reaction with 4-trifluoromethylphenyl isocyanate gives 18% of desired product, mp 274–274.5° C.
IR (KBr): 3350, 1659, 1563, 1559, 1325, 699 cm$^{-1}$;
NMR (DMSO-d$_6$) 5.06 (m, 2H), 7.10–7.59 (m, 19H), 8.33 (s, 1H), 9.08 (s, 2H).
Analysis calculated for C$_{30}$H$_{24}$F$_6$N$_4$O$_2$: C, 61.43; H, 4.12; N, 9.55. Found: C, 61.19; H, 4.29; N, 9.60.

EXAMPLE 26
[S-(R*,R*)] and [R-(R*,R*)]-N-[1,2-diphenyl-2-[[(phenylamino)thioxomethyl]amino]ethyl]-N'-[4-(trifluoromethyl)phenyl]urea

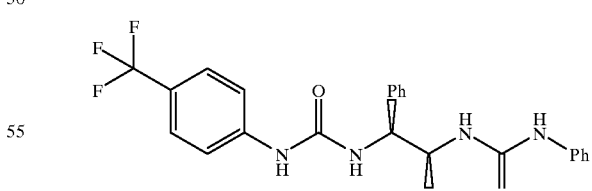

Using Procedure C: Reaction with phenyl isothiocyanate gives 52% of desired white solid, mp 221° C.
IR (KBr): 3320, 1608, 1539, 1497, 1324, 698;
NMR (DMSO-d$_6$): 5.15 (t, 1H, J=8.8 Hz), 5.82 (t, 1H, J=8.8 Hz), 7.04–7.63 (m, 20H), 8.46 (d, 1H, J=8.3 Hz), 9.11 (s, 1H), 9.67 (s, 1H).
Analysis calculated for C$_{29}$H$_{25}$F$_3$N$_4$OS: C, 64.08; H, 4.82; N, 10.31. Found: C, 64.16; H, 4.76; N, 10.10.

EXAMPLE 27

Phenyl [R-(R*,R*)] and [S-(R*,R*)]-N'-cyano-N-[1,2-diphenyl-2-[[[[4-(trifluoromethyl)phenyl]amino]-carbonyl]amino]ethyl]carbamate

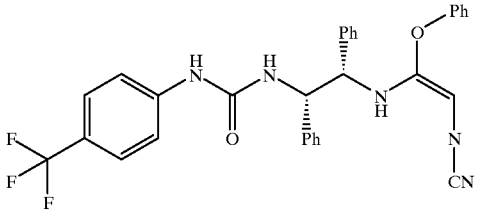

To a suspension of [S-(R*,R*)] and [R-(R*,R*)]-N-(2-amino-1,2-diphenylethyl)-N'-[4-(trifluoromethyl)-phenyl]urea (0.36 g, 0.9 mmol) in isopropanol (10 mL) is added diphenyl cyanocarbonimidate (0.21 g, 0.9 mmol) in one portion. The mixture is heated to reflux for 0.75 hour, cooled to room temperature, and the solid product collected by filtration. The product is washed with diethyl ether (2×) and air dried to provide 0.27 g (56%) of desired white solid, mp 158–158.5° C.

IR (KBr) 3350, 2195, 1695, 1663, 1326, 699 cm$^{-1}$;

NMR (DMSO-d$_6$) 5.13 (m, 2H), 6.81 (m, 1H), 7.14–7.57 (m, 19H), 9.01 (m, 1H), 9.67 (m, 1H).

Analysis calculated for $C_{30}H_{24}F_3N_5O_2 \cdot 0.28H_2O$: C, 65.68; H, 4.51; N, 12.77. Found: C, 65.69; H, 4.35; N, 12.78.

EXAMPLE 28

[R-(R*,R*)] and [S-(R*,R*)]-N-[2-(cyanoamino)-1,2-diphenylethyl]-N'-[4-(trifluoromethyl)phenyl]urea

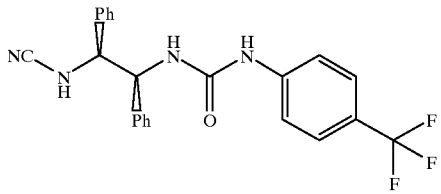

To a suspension of [S-(R*,R*)] and [R-(R*,R*)]-N-(2-amino-1,2-diphenylethyl)-N'-[4-(trifluoromethyl)-phenyl]urea (0.3 g, 0.75 mmol) in water (5 mL) and 1,4-dioxane (5 mL) is added solid sodium bicarbonate (0.06 g, 0.75 mmol) followed by cyanogen bromide (0.1 g, 0.75 nmol). The resulting mixture is stirred 1.5 hour at room temperature before diluting with water and filtering. The solid product is washed with water (2×) and t-butyl-methyl ether (2×). Dry in vacuo at 43° C. for 2 hours, mp 153° C.–154° C.

IR (KBr) 3350, 2225, 1674, 1554, 1326, 1115, 699 cm$^{-1}$;

NMR (DMSO-d$_6$), 4.61 (m, 1H), 5.04 (m, 1H), 7.19 (m, 10H), 7.57 (m, 6H), 9.04 (s, 1H).

Analysis calculated for $C_{23}H_{19}F_3N_4O \cdot 0.31H_2O$: C, 64.24; H, 4.60; N, 13.03. Found: C, 64.24; H, 4.60; N, 12.67.

EXAMPLE 29

Tricyclo[3.3.1.1$^{3,7}$]dec-2-yl [R-(R*,R*)] and [S-(R*,R*)][1,2-diphenyl-2-[[[[4-(trifluoromethyl)-phenyl]amino]carbonyl]amino]ethyl]carbamate

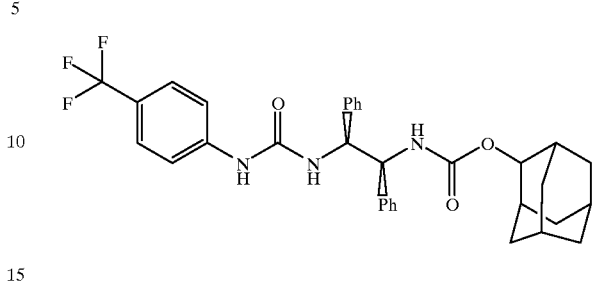

To a suspension of [R-(R*,R*)] and [S-(R*,R*)]-N-(2-amino-1,2-diphenylethyl)-N'-[4-(trifluoromethyl)-phenyl]urea (0.5 g, 1.3 mmol) in dichloromethane (5 mL) is added 2-adamantylchloroformate (0.27 g, 1.3 mmol) followed by triethylamine (0.13 g, 1.3 mmol). The resulting mixture is stirred overnight at room temperature. The solution is concentrated in vacuo and the residue dissolved in diethyl ether. The organic layer is washed with aqueous 2M HCl, saturated aqueous NaCl, and dried over MgSO$_4$. Filtration and concentration in vacuo provides an oil which is purified by flash chromatography (SiO$_2$, ethyl acetate/hexane). The solid product is recrystallized from diethyl ether/hexane to give 0.26 g (38%) desired product, mp 218–219° C.

NMR (DMSO-D$_6$): 1.28–1.92 (m, 14H), 4.57 (br s, 1H), 4.82–5.06 (m, 2H), 6.99–7.83 (m, 15H), 8.98 (s, 1H).

Analysis calculated for $C_{33}H_{34}F_3N_3O_3$: C, 68.62; H, 5.93; N, 7.27. Found: C, 68.28; H, 6.00; N, 7.41.

EXAMPLE 30

[S-(R*,R*)] and [R-(R*,R*)]-N-[1,2-diphenyl-2-[[[[4-(trifluoromethyl)phenyl]amino]carbonyl]amino]-ethyl]benzamide

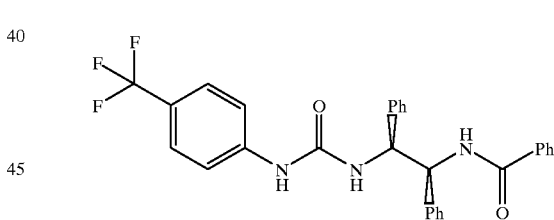

To a suspension of [R-(R*,R*)] and [S-(R*,R*)]-N-(2-amino-1,2-diphenylethyl)-N'-[4-trifluoromethyl) phenyl]urea (0.2 g, 0.5 mmol) in CH$_2$Cl$_2$ (5 mL) is added benzoyl chloride (0.08 g, 0.6 mmol) followed by triethyl amine (0.06 g, 0.6 mmol). The resulting mixture is stirred 2 hours before diluting with diethyl ether and washing with saturated aqueous NaHCO$_3$, saturated aqueous NaCl, and drying over MgSO$_4$. Filtration and concentration provides a residue which is purified by flash chromatography (SiO$_2$, ethyl acetate/hexane). The product is crystallized from diethyl ether/hexane to provide 0.17 g (68%) of white solid, mp 243–245° C.

IR (KBr): 3340, 1690, 1637, 1557, 1539, 1328, 1116, 1068;

NMR (DMSO-d$_6$): 5.16–5.38 (m, 2H), 7.08–7.86 (m, 20H), 8.98 (s, 1H), 9.12 (d, 1H, J=8.4 Hz).

Analysis calculated for $C_{29}H_{24}F_3N_3O_2$: C, 69.18; H, 4.80; N, 8.35. Found: C, 68.80; H, 4.90; N, 8.19.

EXAMPLE 31

[R-(R*,R*)] and [S-(R*,R*)]-N-[1,2-diphenyl-2-[[(tricyclo [3.3.1.1³·⁷]dec-1-ylamino)carbonyl]amino]-ethyl]-N'-[4-(trifluoromethyl)phenyl]urea

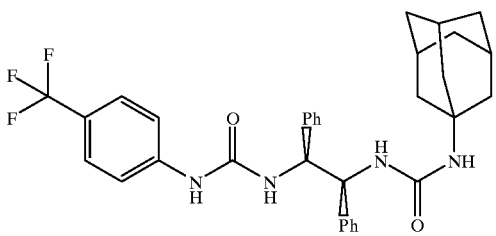

To a solution of 1-adamantyl carboxylic acid (0.04 g, 0.21 mmol) in dry toluene (5 mL) is added phosphoryl azide (0.06 g, 0.21 mmol) and triethyl amine (0.02 g, 0.21 mmol). The resulting mixture is heated to reflux for 4 hours. [R-(R*,R*)] and [S-(R*,R*)]-N-(2-amino-1,2-diphenylethyl)-N'-[4-(trifluoromethyl)-phenyl]urea (0.1 g, 0.25 mmol) is then added and the mixture is allowed to cool to room temperature. The solution is concentrated in vacuo and the residue dissolved in $CH_2Cl_2$ and washed with aqueous 1N NaOH, saturated aqueous NaCl, and dried over $MgSO_4$. Filtration and concentration provides an oil which is purified by flash chromatography ($SiO_2$, EtOAc/hexane eluent). The solid product is triturated in diethyl ether and filtered to provide 0.06 g (48%) of a white solid, mp 236–237° C.

NMR (DMSO-$d_6$): 1.47–1.92 (m, 15H), 4.89 (m, 2H), 5.74 (s, 1H), 6.35 (d, 1H, J=7.8 Hz), 6.90–7.21 (m, 11H), 7.56 (m, 4H), 9.13 (s, 1H).

Analysis calculated for $C_{33}H_{35}F_3N_4O_2 \cdot 0.2H_2O$: C, 68.20; H, 6.16; N, 9.64. Found: C, 68.22; H, 6.16; N, 9.53.

EXAMPLE 32

[S-(R*,R*) and [R-(R*,R*)]-N-[1,2-diphenyl-2-[[[[4-(trifluoromethyl)phenyl]amino]carbonyl]amino]-ethyl] benzeneacetamide

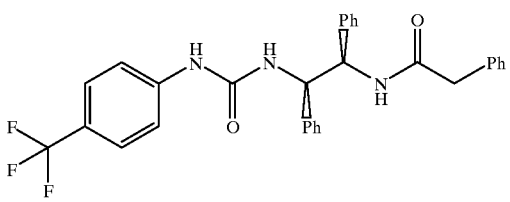

To a solution of [R-(R*,R*)] and [S-(R*,R*)1-N-(2-amino-1,2-diphenylethyl)-N'-[4-(trifluoromethyl) phenyl] urea (0.1 g, 0.25 mmol) in dichloromethane (5 ni) is added phenylacetyl chloride (0.05 g, 0.3 mmol) followed by triethylamine (0.03 g, 0.3 mmol) in one portion. The resulting mixture is stirred 2 hours at room temperature before concentrating in vacuo. The residue is dissolved in diethyl ether and the organic layer washed with aqueous 1N NaOH, aqueous saturated NaCl, and dried over $MgSO_4$. Filtration and concentration gives an oil which is purified by flash chromatography ($SiO_2$, EtOAc/hexane eluent). The resulting solid is recrystallized from ethyl acetate/hexane to give 0.07 g (52*) of desired white solid, mp 233.5–234° C.

NMR (DMSO-$d_6$): 3.46 (dd, 2H, J=26.4, 14 Hz), 5.10 (m, 2H), 6.97–7.19 (m, 20H), 7.57 (s, 4H), 8.82 (d, 1H, J=8.3 Hz), 8.98 (s, 1H).

Analysis calculated for $C_{30}H_{26}F_3N_3O_2 \cdot 0.71H_2O$: C, 67.94; H, 5.21; N, 7.92. Found: C, 67.94; H, 4.84; N, 7.86.

EXAMPLE 33

[S-(R*,R*)] and [R-(R*,R*)]-N-[1,2-diphenyl-2-[[[[4-(trifluoromethyl)phenyl]amino]carbonyl]-amino]ethyl] cyclohexanecarboxamide

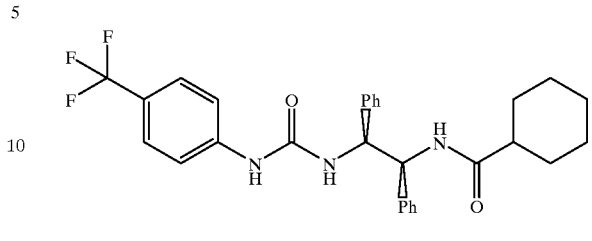

To a solution of [R-(R*,R*)] and [S-(R*,R*)]-N-(2-amino-1,2-diphenylethyl)-N'-[4-(trifluoromethyl) phenyl] urea (0.1 g, 0.25 mmol) in dichloromethane (5 mL) is added triethylamine (0.03 g, 0.3 mmol) followed by cyclohexanecarbonyl chloride (0.04 g, 0.30 mmol). The resulting mixture is stirred 0.75 hour at room temperature before diluting with diethyl ether. The organic layer is washed with aqueous 1N NaOH, aqueous 2M HCl, saturated aqueous NaCl, and dried over $MgSO_4$. Filtration and concentration gives a residue which is purified by flash chromatography ($SiO_2$, EtOAc/hexane eluent). The resulting solid is crystallized from diethyl ether/hexane to provide 0.04 g (32%) of desired white solid, mp 219° C.–220° C.

IR (KBr): 3334, 2930, 1683, 1662, 1556, 1324, 1068, 698 cm$^{-1}$;

NMR (DMSO-$d_6$): 1.12–1.63 (m, 10H), 2.16 (m, 1H), 4.99–5.17 (m, 2H), 6.93 (d, 1H, J=8.2 Hz), 7.06–7.21 (m, 10H), 7.55 (s, 4H), 8.36 (d, 1H, J=8.6 Hz), 9.01 (s, 1H).

Analysis calculated for $C_{29}H_{30}F_3N_3O_2$: C, 68.36; H, 5.93; N, 8.25. Found: C, 68.34; H, 5.88; N, 8.24.

EXAMPLE 34

Methyl [R-(R*,R*)] and [S-(R*,R*)]-2-[[[[1,2-diphenyl-2-[[[[4-(trifluoromethyl)phenyl]amino]carbonyl]amino]-ethyl]amino]carbonyl]amino]cyclohexanecarboxylate

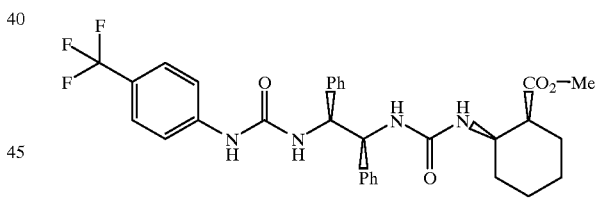

To a solution of methyl trans-1,2-cyclohexanedicarboxylate (0.1 g, 0.5 mmol) in dry toluene (5 mL) is added diphenylphosphoryl azide (0.14 g, 0.50 mmol) and triethyl amine (0.05 g, 0.5 mmol). The resulting mixture is heated to 80° C. for 3 hours before cooling to room temperature and adding [R-(R*,R*)] and [S-(R*,R*)]-N-(2-amino-1,2-diphenylethyl)-N'-[4-(trifluoromethyl) phenyl]-urea (0.23 g, 0.60 mmol) in one portion. The resulting mixture is stirred 2 hours at room temperature. The mixture is concentrated in vacuo and the residue dissolved in 1:1 $Et_2O$/EtOAc. The organic layer is washed with aqueous 2M HCl, saturated aqueous NaCl, and dried over $MgSO_4$. Filtration and concentration gives an oil which is purified by flash chromatography ($SiO_2$, EtOAc/hexane eluent). Obtained 0.07 g (24*) of desired white powder, mp 229–230° C.

NMR (DMSO-$d_6$): 1.1–1.69 (m, 8H), 3.44 (s, 3H), 4.06 (m, 1H), 4.94 (m, 2H), 6.18 (m, 1H), 6.65 (d, 1H, J=7.0 Hz), 6.85 (d, 1H, J=4.9 Hz), 7.06–7.57 (m, 15H), 9.15 (s, 1H).

Analysis calculated for $C_{31}H_{33}F_3N_4O_4 \cdot 0.37H_2O$: C, 63.19; H, 5.77; N, 9.51. Found: C, 63.18; H, 5.55; N, 9.24.

EXAMPLE 35

1,1-dimethylethyl [R-(R*,R*)] and [S-(R*,R*)]-[1,2-diphenyl-3-[[[[4-(trifluoromethyl)phenyl]amino]-carbonyl]amino]ethyl]carbamate

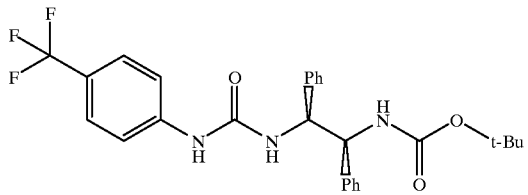

To a suspension of [R-(R*,R*)] and [S-(R*,R*)]-N-(2-amino-1,2-diphenylethyl)-N'-[4-(trifluoromethyl) phenyl] urea (0.1 g, 0.25 mmol) in dioxane (0.5 mL) and water (0.5 mL) is added triethyl amine (0.05 g, 0.53 nmol) followed by 2-(t-butoxycarbonyloxyimino)-2-phenylacetonitrile [BOC-ON®] (0.07 g, 0.28 mmol). The homogeneous mixture is stirred 14 hours at room temperature. The mixture is partitioned between ether (10 mL) and water (5 mL). The layers are separated and the organic layer is washed with water and dried over $MgSO_4$. Filtration and concentration gives an oil which is purified by flash chromatography ($SiO_2$, EtOAc/hexane). The product crystallizes from diethyl ether/hexane to provide 0.05 g (40%) of material, mp 216–217° C. Resolidifies and remelts at 226–227°C.

IR (KBr): 3342, 1670, 1551, 1327, 1111, 700 cm$^{-1}$;

NMR (DMSO-$d_6$): 1.31 (s, 9H), 3.56 (s, 1H), 4.83 (m, 1H), 4.99 (m, 1H), 7.00–7.58 (m, 15H), 8.94 (s, 1H).

Analysis calculated for $C_{27}H_{28}F_3N_3O_3 \cdot 0.2H_2O$: C, 64.46; H, 5.69; N, 8.35. Found: C, 64.49; H, 5.63; N, 8.28.

EXAMPLE 36

Procedure D:

To a solution of [S-(R*,R*)] and [R-(R*,R*)]-N-(2-amino-1,2-diphenylethyl)-N'-cyclohexylurea (0.1 g, 0.3 mmol) in diethyl ether (10 mL) is added the isocyanate or isothiocyanate (0.5 mmol) in one portion. The resulting mixture is stirred 1 hour at room temperature before filtering off the solid product. The product is suspended in hot diethyl ether, filtered, and dried in vacuo at 114° C. for 4 hours.

[R-(R*,R*)] and [S-(R*,R*)]-N-(4-chlorophenyl)-N'-[2-[[(cyclohexylamino)carbonyl]amino]-1,2-diphenyl-ethyl]urea

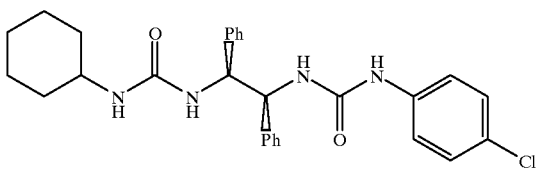

Using Procedure D: Reaction with 4-chlorophenyl isocyanate gives 46% of desired white solid, mp 230–230.5° C.

IR (KBr): 3328, 2931, 1638, 1551, 1402, 1232, 699 cm$^{-1}$;

NMR (DMSO-$d_6$): 1.05–2.51 (m, 10H), 4.93 (m, 2H), 5.93 (d, 1H, J=7.9 Hz), 6.39 (d, 1H, J=7.9 Hz), 6.80 (d, 1H, J=7.3 Hz), 7.01–7.42 (m, 15H), 8.85 (s, 1H).

Analysis calculated for $C_{28}H_{31}ClN_4O_2$: C, 68.49; H, 6.36; N, 11.41. Found: C, 68.25; H, 6.50; N, 11.58.

EXAMPLE 37

[R-(R*,R*)] and [S-(R*,R*)]-N-[2-[[(cyclohexylamino)-carbonyl]amino]-1,2-diphenylethyl]-N'-(4-methoxyphenyl)urea

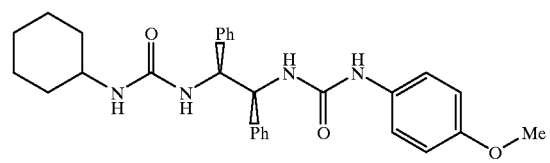

Using Procedure D: Reaction with 4-methoxyphenyl isocyanate gives 42% of desired white product, mp 230° C.

IR (KBr): 3331, 2930, 1641, 1558, 1511, 1240, 700 cm$^{-1}$;

NMR (DMSO-$d_6$): 1.00–1.74 (m, 10H), 3.67 (s, 3H), 4.91 (m, 2H), 5.93 (d, 1H, J=7.9 Hz), 6.37 (d, 1H, J=7.3 Hz), 6.65 (d, 1H, J=7.0 Hz), 6.77 (d, 2H, J=8.9 Hz), 7.00–7.28 (m, 13H), 8.48 (s, 1H).

Analysis calculated for $C_{29}H_{34}N_4O_3$: C, 71.58; H, 7.04; N, 11.51. Found: C, 71.18; H, 7.31; N, 11.69.

EXAMPLE 38

[R-(R*,R*)] and [S-(R*,R*)]-N,N'-(1,2-diphenyl-1,2-ethanediyl)bis[N'-cyclohexyl]urea

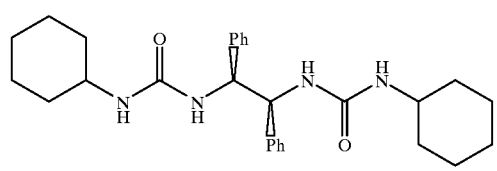

Using Procedure D: Reaction with cyclohexyl isocyanate gives 73% of desired white solid, mp 226–227° C.

IR (KBr): 3337, 2853, 1635, 1558, 699 cm$^{-1}$.

NMR (DMSO-$d_6$): 1.00–1.77 (m, 20H), 4.83 (m, 2H), 5.95 (d, 2H, J=7.9 Hz), 6.30 (m, 2H), 6.95–7.34 (m, 12H).

Analysis calculated for $C_{28}H_{38}N_4O_2$: C, 72.69; H, 8.28; N, 12.11. Found: C, 73.01; H, 8.37; N, 12.31.

EXAMPLE 39

[R-(R*,R*)] and [S-(R*,R*)]-N-(2-chlorophenyl)-N'-[2-[[(cyclohexylamino)carbonyl]amino]-1,2-diphenyl-ethyl]urea

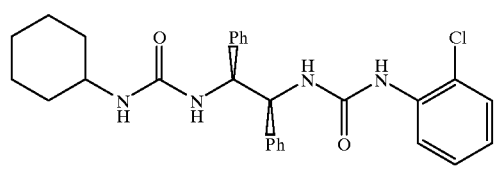

Using Procedure D: Reaction with 2-chlorophenyl isocyanate gives 75% of desired white solid, mp 225.5–226° C.

NMR (DMSO-$d_6$): 0.98–1.71 (m, 10H), 4.92 (m, 2H), 5.93 (d, 1H, J=7.9 Hz), 6.36 (m, 1H), 6.89–7.39 (m, 14H), 7.71 (m, 1H), 8.15–8.23 (m, 2H).

Analysis calculated for $C_{28}H_{31}ClN_4O_2$: C, 68.49; H, 6.36; N, 11.41. Found: C, 68.28; H, 6.35; N, 11.29.

EXAMPLE 40

[R-(R*,R*)] and [S-(R*,R*)]-N-(3-chlorophenyl)-N'-[2-[[[(cyclohexylamino)carbonyl]amino]-1,2-diphenylethyl]urea

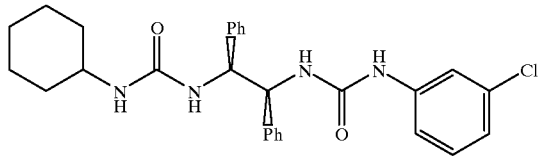

Using Procedure D: Reaction with 3-chlorophenyl isocyanate gives 67% of desired white powder, mp 224–225° C.
IR (KBr): 3332, 2931, 1637, 1592, 1551, 1230, 699 cm$^{-1}$;
NMR (DMSO-d$_6$): 1.00–1.67 (m, 10H), 4.92 (m, 2H), 5.93 (d, 1H, J=7.9 Hz), 6.39 (m, 1H), 6.89–7.14 (m, 16H), 8.93 (s, 1H).
Analysis calculated for C$_{28}$H$_{31}$ClN$_4$O$_2$: C, 68.49; H, 6.36; N, 11.41. Found: C, 68.30; H, 6.27; N, 11.25.

EXAMPLE 41

[R-(R*,R*)] and [S-(R*,R*)]-N-[2-[[[(cyclohexylamino)carbonyl]amino]-1,2-diphenylethyl]-N'-(2-methoxyphenyl)urea

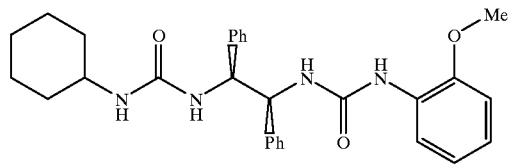

Using Procedure D: Reaction with 2-methoxyphenyl isocyanate gives 42* of desired white solid, mp 229–230° C.
IR (KBr): 3354, 2931, 1643, 1544, 1250, 699 cm$^{-1}$;
NMR (DMSO-d$_6$): 0.97–1.71 (m, 10H), 3.83 (s, 3H), 4.9 (m, 2H), 5.93 (d, 1H, J=7.9 Hz), 6.33 (m, 1H), 6.76–7.19 (m, 15H), 8.09 (m, 2H).
Analysis calculated for C$_{29}$H$_{34}$N$_4$O$_3$: C, 71.58; H, 7.04; N, 11.51. Found: C, 71.34; H, 7.05; N, 11.43.

EXAMPLE 42

[R-(R*,R*)] and [S-(R*,R*)]-N-cyclohexyl-N'-[2-[[[(3-methoxyphenyl)amino]carbonyl]amino]-1,2-diphenylethyl]urea

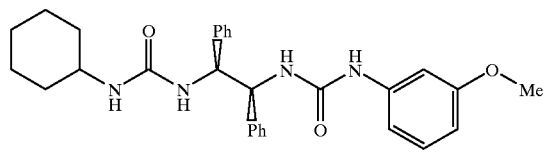

Using Procedure D: Reaction with 3-methoxy phenyl isocyanate gives 50% of desired white product, mp 214–214.5° C.
IR (KBr): 3335, 2931, 1638, 1605, 1559, 699 cm$^{-1}$;
NMR (DMSO-d$_6$): 0.99–1.74 (m, 10H), 3.69 (s, 3H), 4.94 (m, 2H), 5.93 (d, 1H, J=7.9 Hz), 6.43 (m, 2H), 6.80 (m, 2H), 6.99–7.22 (m, 13H), 8.89 (s, 1H).
Analysis calculated for C$_{29}$H$_{34}$N$_4$O$_3$: C, 71.58; H, 7.09; N, 11.51. Found: C, 71.42; H, 6.95; N, 11.51.

EXAMPLE 43

[S-(R*,R*)] and [R-(R*,R*)]-N-cyclohexyl-N'-[2-[[[(4-cyanophenyl)amino]thioxomethyl]amino]-1,2-diphenylethyl]urea

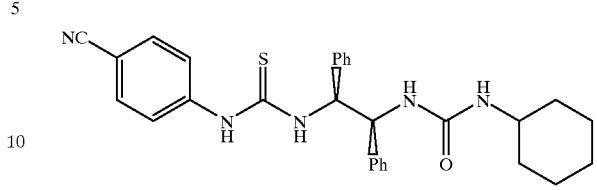

Using Procedure D: Reaction with 4-cyanophenyl isothiocyanate gives 33% of desired white powder, mp 209.5–210° C.
IR (KBr): 3298, 2930, 2224, 1636, 1539, 1318, 699 cm$^{-1}$;
NMR (DMSO-d$_6$): 1.15–1.62 (m, 10H), 5.02 (t, 1H, J=9.1 Hz), 5.69 (m, 1H), 5.99 (d, 1H, J=7.7 Hz), 6.17 (d, 1H, J=7.7 Hz), 7.05–7.20 (m, 11H), 7.73 (s, 4H), 8.81 (s, 1H), 10.09 (s, 1H).
Analysis calculated for C$_{29}$H$_{31}$N$_5$OS.0.3H$_2$O: C, 69.24; H, 6.33; N, 13.92. Found: C, 69.20; H, 6.25; N, 13.70.

EXAMPLE 44

Tricyclo[3.3.1.1$^{3,7}$]dec-2-yl[R-(R*,R*)] and [S-(R*,R*)]-[2-[[(cyclohexylamino)carbonyl]amino]-1,2-diphenylethyl]carbamate

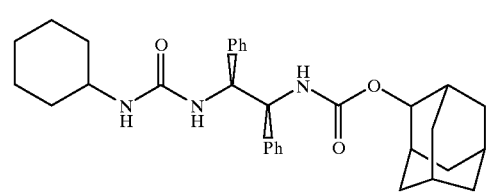

To a suspension of [S-(R*,R*)] and [R-(R*,R*)]-N-(2-amino-1,2-diphenylethyl)-N'-cyclohexylurea (0.08 g, 0.24 mmol) in dichloromethane (5 mL) is added 2-adamantylchloroformate (0.05 g, 0.24 mmol) followed by triethylamine (0.02 g, 0.24 mmol). The resulting mixture is stirred overnight at room temperature. The solution is concentrated in vacuo and the residue dissolved in diethyl ether. The organic is washed with aqueous 2M HCl, saturated aqueous NaCl, and dried over MgSO$_4$. Filtration and concentration in vacuo provides an oil which is purified by flash chromatography (SiO$_2$, EtOAc/hexane). The resulting foam crystallizes from hexane to provide 0.05 g (42%) of desired product, mp 132–141° C.
IR (KBr): 3336, 2928, 1700, 1636, 1558, 1242, 698 cm$^{-1}$;
NMR (DMSO-d$_6$): 1.02–1.96 (m, 24H), 4.54 (m, 1H), 4.73–4.96 (m, 2H), 5.81 (d, 1H, J=7.9 Hz), 6.44 (d, 1H, J=8.5 Hz), 7.09–7.16 (m, 11H), 7.63 (d, 1H, J=8.5 Hz).
Analysis calculated for C$_{32}$H$_{41}$N$_3$O$_3$.0.26H$_2$O: C, 73.86; H, 8.04; N, 8.07. Found: C, 73.85; H, 8.03; N, 7.86.

EXAMPLE 45

Procedure E:

To a solution of [R-(R*,R*)] and [S-(R*,R*)]-N-(2-amino-1,2-diphenylethyl)-N'-[4-chlorophenyl)urea (0.1 g, 0.27 mmol) in diethyl ether (10 mL) is added the appropriate isocyanate (0.27 mmol) in one portion. The resulting mixture is stirred 1 hour at room temperature before filtering off the solid product. The solid is suspended in hot diethyl ether, filtered, and dried in vacuo at 114° C. for 4 hours.

[R-(R*,R*)] and [S-(R*,R*)]-N-(4-chlorophenyl)-N'-[2-[[(1-naphthalenylamino)carbonyl]amino]-1,2-diphenylethyl]urea

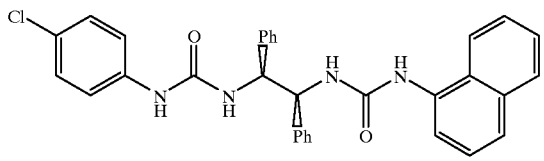

Using Procedure E: Reaction with 1-napthyl isocyanate gives 63% of desired white solid, mp 238.5–239° C.

IR (KBr): 3330, 1650, 1556, 1399, 699 cm$^{-1}$;

NMR (DMSO-d$_6$): 5.07 (m, 2H), 6.94–7.57 (m, 20H), 7.85–8.05 (m, 3H), 8.71 (s, 1H), 8.81 (s, 1H).

Analysis calculated for $C_{32}H_{27}ClN_4O_2$: C, 71.84; H, 5.09; N, 10.47. Found: C, 71.66; H, 4.97; N. 10.37.

EXAMPLE 46

[R-(R*,R*)] and [S-(R*,R*)]-N-[[[2-[[[(4-chlorophenyl)amino]carbonyl]amino]-1,2-diphenylethyl]amino]-carbonyl]-4-methyl-benzenesulfonamide

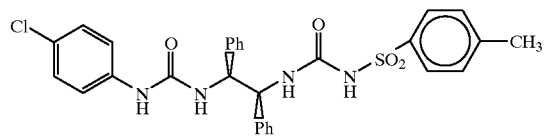

Using Procedure E: Reaction with 4-methylbenzenesulfonyl isocyanate gives 52% of desired product, mp 213–214° C.

IR (KBr): 3360, 1653, 1542, 1492, 669 cm$^{-1}$;

NMR (DMSO-d$_6$): 2.32 (s, 3H), 4.82–5.02 (m, 2H), 6.84–7.73 (m, 19H), 8.62 (s, 1H).

Analysis calculated for $C_{29}H_{27}ClN_4O_4S$: C, 61.86; H, 4.83; N, 9.85. Found: C, 61.49; H, 4.80; N, 9.85.

EXAMPLE 47

[R-(R*,R*)] and [S-(R*,R*)]-N-[[[2-[[[4-chlorophenyl)amino]carbonyl]amino]-1,2-diphenylethyl]amino]-carbonyl]benzenesulfonamide

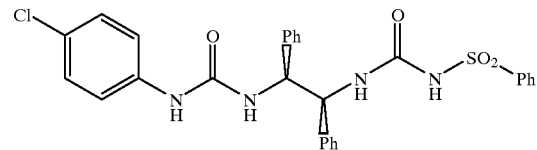

Using Procedure E: Reaction with benzenesulfonyl isocyanate gives 88% of desired white solid, mp 216–217.5° C.

IR (KBr): 3368, 1699, 1662, 1545, 1492, 1162, 699 cm$^{-1}$;

NMR (DMSO-d$_6$): 4.81–5.02 (m, 2H), 6.85–7.85 (m, 21H), 8.66 (s, 1H), 10.7 (s, 1H).

Analysis calculated for $C_{28}H_{25}ClN_4O_4S$: C, 61.25; H, 4.59; N, 10.20. Found: C, 61.09; H, 4.64; N, 10.18.

EXAMPLE 48

[S-(R*,R*)] and [R-(R*,R*)]-N-(4-chlorophenyl)-N'-[1,2-diphenyl-2-[[(phenylamino)carbonyl]amino]ethyl]-urea

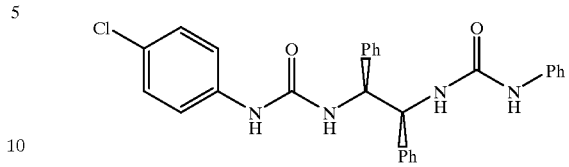

Using Procedure E: Reaction with phenyl isocyanate gives 70% of desired white solid, mp 243–245° C.

IR (KBr): 3328, 1653, 1597, 1552, 1236, 698 cm$^{-1}$;

NMR (DMSO-d$_6$): 5.04 (m, 2H), 6.85–7.42 (m, 21H), 8.62 (s, 1H), 8.79 (s, 1H).

Analysis calculated for $C_{28}H_{25}ClN_4O_2$: C, 69.34; H, 5.20; N, 11.55. Found: C, 69.15; H, 5.07; N, 11.34.

EXAMPLE 49

[S-(R*,R*)] and [R-(R*,R*)]-N-(4-chlorophenyl)-N'-[2-[[[(4-cyanophenyl)amino]thioxomethyl]amino]-1,2-diphenylethyl]urea

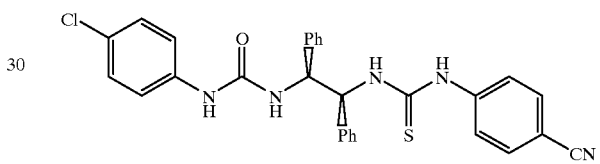

Using Procedure E: Reaction with 4-cyanophenyl isothiocyanate yields 56% of desired white powder, mp 187–188.5° C.

IR (KBr): 3423, 1654, 1493, 1239, 698 cm$^{-1}$;

NMR (DMSO-d$_6$): 5.14 (m, 1H), 5.71 (m, 1H), 6.96–7.69 (m, 20H), 8.79 (s, 1H), 8.88 (d, 1H, J=8.1 Hz).

Analysis calculated for $C_{29}H_{24}ClN_5O_5$: C, 66.21; H, 4.60; N, 13.31. Found: C, 66.59; H, 4.80; N, 13.48.

EXAMPLE 50

[S-(R*,R*)] and [R-(R*,R*)]-N-(4-chlorophenyl)-N'-[2-[[[4-(methylthio)phenyl]amino)carbonyl]amino]-1,2-diphenylethyl]urea

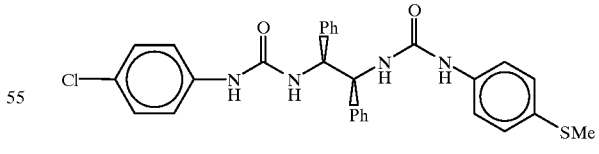

Using Procedure E: Reaction with 4-methylthiophenyl isocyanate gives 87% of desired white product, mp 258–259° C.

IR (KBr): 3341, 1649, 1594, 1545, 1492, 1235, 699 cm$^{-1}$;

NMR (DMSO-d$_6$): 2.35 (s, 3H), 5.05 (m, 2H), 6.81–7.48 (m, 20H), 8.65 (s, 1H), 8.81 (s, 1H).

Analysis calculated for $C_{29}H_{27}ClN_4O_2S \cdot 0.5H_2O$: C, 64.49; H, 5.23; N, 10.37. Found: C, 64.61; H, 5.08; N, 10.45.

EXAMPLE 51

[S-(R*,R*)] and [R-(R*,R*)]-N-(4-chlorophenyl)-N'-[2-[[[[4-(methylsulfonyl)phenyl]amino]carbonyl]amino]-1,2-diphenylethyl]urea

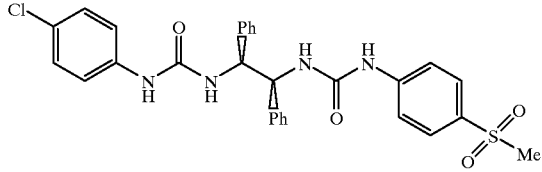

To a suspension of [R-(R*,R*)] and [S-(R*,R*)-N-(4-chlorophenyl)-N'-[2-[[[[4-(methylsulfonyl)phenyl]-amino]carbonyl]amino]-1,2-diphenylethyl]urea (0.2 g, 0.38 mmol) in methanol (10 mL) is added m-chloroperbenzoic acid (0.84 g, 5.1 mmol) in one portion. The resulting mixture is stirred overnight at room temperature. The solution is filtered and the supernate is concentrated in vacuo to yield a yellow oil. The oil is purified by flash chromatography (SiO$_2$, EtOAc/hexane) to yield 0.09 g (42%) of desired white solid, mp 246° C.

IR (KBr): 3355, 1657, 1593, 1544, 1492, 1145, 700 cm$^{-1}$;

NMR (DMSO-d$_6$): 3.12 (s, 3H), 5.03 (m, 2H), 6.93–7.75 (m, 20H), 8.77 (s, 1H), 9.19 (s, 1H).

Analysis calculated for C$_{29}$H$_{27}$ClN$_4$O$_4$S.0.5H$_2$O: C, 60.89; H, 4.93; N, 9.79. Found: C, 60.76; H, 4.71; N, 9.51.

EXAMPLE 52

[R-(R*,R*)] and [S-(R*,R*)]-N-[2-[[[(4-chlorophenyl)-amino]carbonyl]amino]-1,2-diphenylethyl]-4-methylbenzenesulfonamide

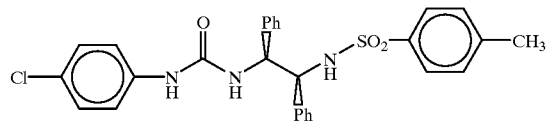

To a solution of [S-(R*,R*)] and [R-(R*,R*)]-N-(2-amino-1,2-diphenylethyl)-N'-(4-chlorophenyl)urea (0.1 g, 0.27 mmol) in dichloromethane (7 mL) is added pyridine (0.02 g, 0.27 mmol) followed by p-toluenesulfonyl chloride (0.05 g, 0.27 mmol) and 4-dimethylaminopyridine (catalytic). The resulting mixture is stirred overnight at room temperature. The mixture is concentrated in vacuo and the residue dissolved in 1:1 EtOAc/Et$_2$O, washed with saturated aqueous NaCl, and dried (MgSO$_4$). Filtration and concentration gives an oil which is purified by flash chromatography (SiO$_2$, EtOAc/hexane). The solid product is suspended in hot diethyl ether and filtered to give 0.081 g (59n) of desired white solid, mp 235–236° C.

IR (KBr): 3380, 1677, 1545, 1493, 1307, 1154, 697 cm$^{-1}$;

NMR (DMSO-d$_6$): 2.20 (s, 3H), 4.51 (m, 1H), 4.93 (m, 1H), 6.80–7.39 (m, 19H), 8.39 (d, 1H, J=9.0 Hz), 8.78 (s, 1H).

Analysis calculated for C$_{28}$H$_{26}$ClN$_3$O$_3$S: C, 64.67; H, 5.04; N, 8.08. Found: C, 64.52; H, 4.82; N, 7.73.

EXAMPLE 53

[R-(R*,R*)] and [S-(R*,R*)]-N-[2-[[[(4-chlorophenyl)-amino]carbonyl]amino]-1,2-diphenylethyl]-1H-Indole-3-acetamide

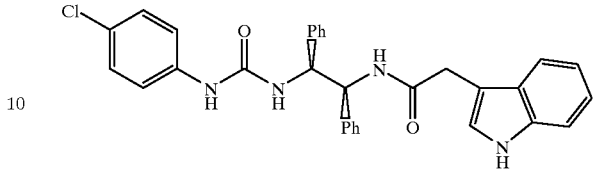

To a solution of [S-(R*,R*)] and [R-(R*,R*)]-N-(2-amino-1,2-diphenylethyl)-N'-(4-chlorophenyl)urea (0.1 g, 0.27 mmol) in dichloromethane (5 1L) is added triethyl amine (0.03 g, 0.27 nmol) followed by indole-3-acetic acid chloride (0.05 g, 0.27 mmol). The mixture is stirred 1.5 hours at room temperature before diluting with diethyl ether and washing with aqueous 2M HCl, aqueous 1M NaOH, saturated aqueous NaCl, and drying (MgSO$_4$). Filtration and concentration gives an oil which is purified by flash chromatography (SiO$_2$, EtOAc/hexane eluent) to provide 0.05 g (33*) of desired product, mp 224–227° C.

IR (KBr): 3360, 1549, 1492, 1226, 698 cm$^{-1}$;

NMR (DMSO-d$_6$): 3.56 (s, 2H), 5.07 (m, 2H), 6.78–7.45 (m, 20H), 8.65 (m, 2H), 10.81 (s, 1H).

Analysis calculated for C$_{31}$H$_{27}$ClN$_4$O$_2$.0.5H$_2$O: C, 69.98; H, 5.30; N, 10.53. Found: C, 69.65; H, 5.41; N, 10.56.

EXAMPLE 54

Procedure F:

To a solution of [S-(R*,R*)] and [R-(R*,R*)]-N-[[(2-amino-1,2-diphenylethyl)amino]carbonyl]-4-methylbenzenesulfonamide (0.3 g, 0.7 mmol) is added the appropriate isocyanate (0.7 mmol) in one portion. The resulting mixture is stirred 1 hour at room temperature before filtering off the solid product. The product is purified by the method described in individual examples.

[R-(R*,R*)] and [S-(R*,R*)]-4-methyl-N-[[[2-[[[(4-methylphenyl)amino]carbonyl]amino]-1,2-diphenylethyl]amino]carbonyl]benzenesulfonamide

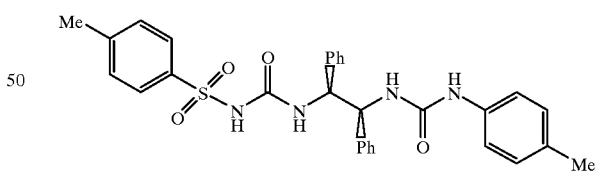

Using Procedure F: Reaction with 4-methylphenyl isocyanate gives 21% of desired product after purifying by flash chromatography (SiO$_2$, 18:1:1 EtOAc/H$_2$O/HCO$_2$H eluent) then suspending the solid product in hot diethyl ether and filtering. Dry in vacuo at 114° C. for 4 hours.

IR (KBr): 3365, 1716, 1662, 1541, 1161, 700 cm$^{-1}$;

NMR (DMSO-d$_6$): 2.21 (s, 3H), 2.31 (s, 3H), 4.92 (m, 2H), 6.79 (d, 1H, J=8.5 Hz), 7.01–7.27 (m, 18H), 7.67 (m, 2H), 8.39 (s, 1H).

Analysis calculated for C$_{30}$H$_{30}$N$_4$O$_4$S.0.5H$_2$O: C, 65.32; H, 5.66; N, 10.16. Found: C, 64.99; H, 5.36; N, 9.85.

EXAMPLE 55

[S-(R*,R*)] and [R-(R*,R*)]-N-[[[2-[[[(2,4-difluorophenyl)amino]carbonyl]amino]-1,2-diphenylethyl]amino]carbonyl]-4-methyl-benzenesulfonamide Using Procedure F: Reaction with 2,4-difluorophenyl isocyanate gives 54% of desired product after filtering solid product, washing with ethyl acetate, and drying in vacuo for 1 hour at 114° C., mp 211–214° C.

IR (KBr): 3370, 1662, 1551, 1160, 700 cm$^{-1}$;

NMR (DMSO-d$_6$): 2.34 (s, 3H), 4.91 (m, 2H), 6.95–7.31 (m, 18H), 7.70 (d, 2H, J=8.1 Hz), 8.08 (m, 1H).

Analysis calculated for $C_{29}H_{26}F_2N_4O_4S$: C, 61.69; H, 4.64; N, 9.92. Found: C, 61.73; H, 4.61; N, 9.89.

EXAMPLE 56

[S-(R*,R*)] and [R-(R*,R*)]-N-[[[2-diphenyl-2-[[(phenylamino)carbonyl]amino]ethyl]amino]carbonyl]-4-methyl-benzenesulfonamide Using Procedure F: Reaction with phenyl isocyanate gives 27% yield of desired white solid after suspending in hot diethyl ether, filtering, and drying in vacuo at 114° C. for 6 hours, mp 210–211° C.

IR (KBr): 3375, 1655, 1541, 1160, 701 cm$^{-1}$;

NMR (DMSO-d$_6$): 2.31 (s, 3H), 4.86 (m, 2H), 6.90–7.38 (m, 19H), 7.68 (d, 2H, J=8.0 Hz), 8.50 (s, 1H), 10.61 (br s, 1H).

Analysis calculated for $C_{29}H_{28}N_4O_4S \cdot 1.4H_2O$: C, 62.87; H, 5.61; N, 10.11. Found: C, 62.87; H, 5.22; N, 9.94.

EXAMPLE 57

[S-(R*,R*)] and [R-(R*,R*)]-N-[[[2-[[(cyclohexylamino)carbonyl]amino]-1,2-diphenylethyl]amino]carbonyl]-4-methyl-benzenesulfonamide Using Procedure F: Reaction with cyclohexyl isocyanate gives 31% of desired white solid after suspending in hot diethyl ether, filtering, and drying the solid in vacuo at 114° C. for 4 hours, mp 188–191° C.

IR (KBr): 3313, 2929, 1624, 1570, 1164, 668 cm$^{-1}$;

NMR (DMSO-d$_6$): 1.01–1.78 (m, 10H), 2.36 (s, 3H), 4.81 (m, 2H), 5.90 (d, 1H, J=7.9 Hz), 6.37 (d, 1H, J=8.3 Hz), 6.88–7.36 (m, 14H), 6.70 (m, 2H), 10.65 (m, 1H).

Analysis calculated for $C_{29}H_{34}N_4O_4S \cdot 0.5H_2O$: C, 64.07; H, 6.49; N, 10.30. Found: C, 64.04; H, 6.20; N, 10.15.

EXAMPLE 58

[R-(R*,R*)] and [S-(R*,R*)]-N-[[[2-[[[(4-methoxyphenyl)amino]carbonyl]amino]-1,2-diphenylethyl]amino]carbonyl]-4-methyl-benzenesulfonamide Using Procedure F: Reaction with 4-methoxyphenyl isocyanate gives 15% yield of desired product after purifying by flash chromatography (SiO$_2$, 18:1:1 EtOAc/H$_2$O/HCO$_2$H eluent) followed by suspension of the solid product in hot diethyl ether and filtering. Dried in vacuo at 114° C. for 4 hours, mp 163–164° C.

IR (KBr): 3370, 1693, 1653, 1512, 1159, 701 cm$^{-1}$;

NMR (DMSO-d$_6$): 2.32 (s, 3H), 3.69 (s, 3H), 4.91 (m, 2H), 6.71–7.34 (m, 19H), 7.68 (d, 2H, J=8.1 Hz), 8.32 (s, 1H)

Analysis calculated for $C_{30}H_{30}N_4O_5S \cdot 0.91H_2O$: C, 62.66; H, 5.58; N, 9.74. Found: C, 62.28; H, 5.18; N, 9.60.

EXAMPLE 59

[R-(R*,R*)] and [S-(R*,R*)]-N-[[[2-[[[3-chlorophenyl)amino]carbonyl]amino]-1,2-diphenylethyl]amino]carbonyl]-4-methyl-benzenesulfonamide Using Procedure F: Reaction with 3-chlorophenyl isocyanate gives 32% of desired product after purifying by flash chromatography (SiO$_2$, EtOAc/hexane eluent) followed by suspension of the solid product in diethyl ether and filtering. Dry in vacuo at 114° C. for 8 hours, mp 197–200° C.

NMR (DMSO-d$_6$): 3.32 (s, 3H), 4.91 (m, 2H), 6.89–7.72 (m, 20H), 8.73 (s, 1H), 10.61 (br s, 1H).

Analysis calculated for $C_{29}H_{27}ClN_4O_4S \cdot 0.5H_2O$: C, 60.89; H, 4.93; N, 9.79. Found: C, 61.11; H, 4.87; N, 9.64.

EXAMPLE 60

[S-(R*,R*)]-N,N'-[[(1,2-diphenyl-1,2-ethanediyl)amino]carbonyl]bis[4-methyl]benzenesulfonamide To a solution of (−)-[S-(R*,R*))-1,2-diamino-1,2-diphenylethane (1.0 g, 4.7 mmol) in diethyl ether (20 mL) is added a solution of p-toluene sulfonyl isocyanate (0.92 g, 4.7 mmol) in diethyl ether (15 mL) dropwise. After the addition is complete the mixture is stirred 0.5 hour before the solid product is collected by filtration. The solid is washed with diethyl ether (3×) and dried in vacuo at 114° C. to provide 1.8 g (62%) of desired product, mp 204–207° C.

NMR (DMSO-d$_6$): 2.37 (s, 6H), 4.82 (m, 2H), 6.90–7.75 (m, 22H).

Analysis calculated for C$_{30}$H$_{30}$N$_4$O$_6$S$_2$: C, 59.39; H, 4.98; N, 9.23. Found: C, 59.02; H, 4.66; N, 9.00.

EXAMPLE 61

[R-(R*,R*)]-N,N'-[[(1,2-diphenyl-1,2-ethanediyl)amino]-carbonyl]bis[4-methyl-benzenefulfonamide]

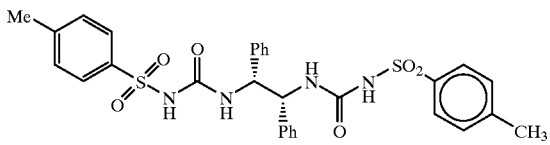

To a solution of (+)-[R-(R*,R*)]-1,2-diamino-1,2-diphenylethane (1.0 g, 4.7 mmol) in diethyl ether (20 mL) is added a solution of p-toluenesulfonyl isocyanate (0.92 g, 4.7 mmol) in diethyl ether (15 mL) dropwise. After the addition is complete the mixture is stirred 0.5 hour before the solid product is collected by filtration. The solid is washed with diethyl ether (3×) and dried in vacuo to provide 1.8 g (62%) of desired product, mp 204–206° C.

NMR (DMSO-d$_6$): 2.37 (s, 6H), 4.81 (m, 2H), 6.89–7.74 (m, 22H).

Analysis calculated for C$_{30}$H$_{30}$N$_4$O$_6$S$_2$: C, 59.39; H, 4.98; N, 9.23. Found: C, 59.02; H, 4.66; N, 9.00.

EXAMPLE 62

Procedure G:

To a solution of (−)-[R-(R*,R*)]-N-(2-amino-1,2-diphenylethyl)-N'-(4-chlorophenyl)urea (0.41 mmol) in dichloromethane (10 mL) is added the appropriate isocyanate (0.41 mmol) in one portion. The resulting mixture is stirred 1 hour at room temperature before filtering off the solid product. The product is suspended in hot diethyl ether, filtered, and dried in vacuo at 114° C. for 4 hours.

(−)-[R-(R*,R*)]-N-[[[2-[[[(4-chlorophenyl)amino]-carbonyl]amino]-1,2-diphenylethyl]amino]carbonyl]-4-methyl-benzenesulfonamide

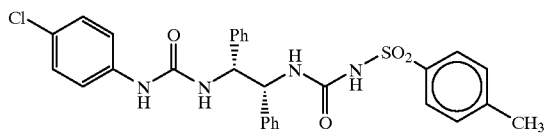

Using Procedure G: Reaction with 4-methyl-benzenesulfonyl isocyanate gives 0.18 g (85*) of desired white solid, mp 200–201° C.

IR (KBr): 3367, 1668, 1546, 1492, 1160, 701 cm$^{-1}$;

NMR (DMSO-d$_6$): 2.32 (s, 3H), 4.85 (m, 2H), 6.84–7.43 (m, 18H), 7.71 (d, 2H, J=8.2 Hz), 8.67 (s, 1H), 10.65 (s, 1H).

Analysis calculated for C$_{29}$H$_{27}$ClN$_4$O$_4$S: C, 61.86; H, 4.83; N, 9.95. Found: C, 61.50; H, 4.98; N, 9.79.

[α]$_D^{25}$=−24.9 (c=1, MeOH).

EXAMPLE 63

(−)-[R-(R*,R*)]-N-(4-chlorophenyl)-N'-[1,2-diphenyl-2-[[[[4-(trifluoromethyl)phenyl]amino]erbonyl]amino]-ethyl]urea

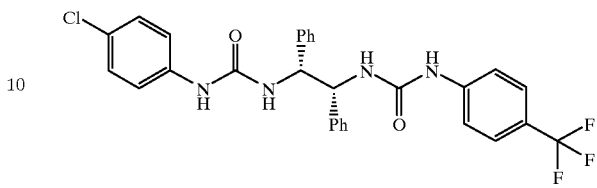

Using Procedure G: Reaction with 4-trifluoromethyl phenyl isocyanate gives 0.17 g (73%) of desired white solid, mp 229.5–230° C.

IR (KBr): 3339, 1653, 1554, 1493, 1326, 1120, 700 cm$^{-1}$;

NMR (DMSO-d$_6$): 5.01 (m, 2H), 6.91–7.59 (m, 20H), 8.76 (s, 1H), 9.06 (s, 1H).

Analysis calculated for C$_{29}$H$_{24}$ClF$_3$N$_4$O$_2$: C, 62.99; H, 4.37; N, 10.13. Found: C, 62.91; H, 4.45; N, 10.05.

[α]$_D^{25}$=−6.6 (c=1, MeOH).

EXAMPLE 64

Procedure H:

To a solution of (+)-[S-(R*,R*)]-N-(2-amino-1,2-diphenylethyl)-N'-(4-chlorophenyl)urea 0.15 g (0.41 mmol) in dichloromethane (10 mL) is added the appropriate isocyanate (0.41 mmol) in one portion. The resulting mixture is stirred 1 hour at room temperature before filtering off the solid product. The product is suspended in hot diethyl ether, filtered, and dried in vacuo for 5 hours.

(+)-[S-(R*,R*)]-N-[[[2-[[[(4-chlorophenyl)amino]-carbonyl]amino]-1,2-diphenylethyl]amino]carbonyl]-4-methyl-urea

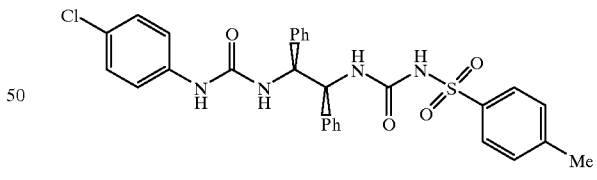

Using Procedure H: Reaction with 4-methyl-benzenesulfonyl isocyanate gives 98% of desired white solid, mp 149–150.5° C.

IR (KBr): 3365, 1667, 1546, 1493, 1160 cm$^{-1}$;

NMR (DMSO-d$_6$): 2.32 (s, 3H), 4.86 (m, 2H), 6.83–7.41 (m, 18H), 7.72 (d, 2H, J=8.2 Hz), 8.67 (s, 1H), 10.63 (s, 1H).

Analysis calculated for C$_{29}$H$_{27}$ClN$_4$O$_4$S: C, 61.86; H, 4.83; N, 9.95. Found: C, 62.17; H, 5.13; N, 9.70.

[α]$_D^{25}$=+22.6 (c=1, MeOH).

EXAMPLE 65

(+)-[S-(R*,R*)]-N-(4-chlorophenyl)-N'-[1,2-diphenyl]-2-[[[[4-(trifluoromethyl)phenyl]amino]carbonyl]amino]-ethyl]urea

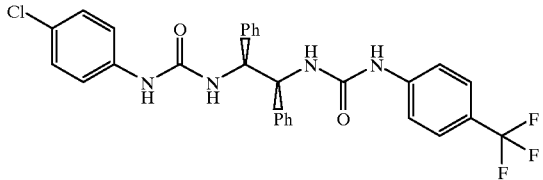

Using Procedure H: Reaction with 4-trifluoromethyl phenyl isocyanate gives 93% of desired white solid, mp 231–233° C.

IR (KBr): 3348, 1653, 1554, 1493, 1326, 1118, 700 cm$^{-1}$;

NMR (DMSO-d$_6$): 5.02 (m, 2H), 6.91–7.60 (m, 20H), 8.76 (s, 1H), 9.06 (s, 1H).

Analysis calculated for C$_{29}$H$_{24}$ClF$_3$N$_4$O$_2$: C, 62.99; H, 4.37; N, 10.13. Found: C, 62.78; H, 4.16; N, 10.08.

[α]$_D^{25}$=+6.1 (c=1, MeOH).

EXAMPLE 66

Procedure I:

To a solution of ethyl (+)-[S-(R*,R*)]-3-[[[(2-amino-1,2-diphenylethyl)amino]carbonyl]amino)-benzoic acid (0.2 g, 0.49 mmol) in dichloromethane (5 mL) is added the appropriate isocyanate (0.49 mmol) in one portion. The resulting mixture is stirred 1 hour at room temperaure before concentrating in vacuo. The resulting oil is dissolved in 1:1 EtOAc:Et$_2$O and precipitated with hexane. The solid is filtered, washed with hexane, and dried in vacuo at 114° C. for 4 hours.

Ethyl-(–)-[S-(R*,R*)]-3-[[[[2-[[[[4-methylphenyl)-sulfonyl]amino]carbonyl]amino]-1,2-diphenylethyl]-amino]carbonyl]amino]benzoate

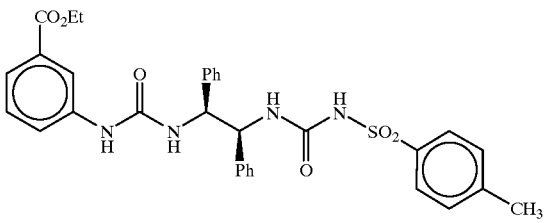

Using Procedure I: Reaction with 4-methylbenzenesulfonyl isocyanate gives 76% of desired white solid, mp 195–196° C.

IR (KBr): 3377, 1685, 1543, 1238, 1161, 700 cm$^{-1}$.

NMR (DMSO-d$_6$): δ 1.31 (t, 3H, J=7.1 Hz), 2.31 (s, 3H), 4.29 (q, 2H, J=14.2, 7.1 Hz), 4.83–5.04 (m, 2H), 6.82–7.72 (m, 19H), 8.10 (s, 1H), 8.81 (s, 1H), 10.61 (s, 1H).

Analysis calculated for C$_{32}$H$_{32}$N$_4$O$_6$S: C, 64,23; H, 5.44; N, 9.44. Found: C, 63.98; H, 5.37; N, 9.33.

[α]$_D^{25}$=–2.4° C. (c=1, DMF).

EXAMPLE 67

(–)-[S-(R*,R*)]-3-[[[[2-[[[[(4-methylphenyl)sulfonyl]-amino]carbonyl]amino]-1,2-diphenylethyl]amino]-carbonyl]amino]benzoic acid

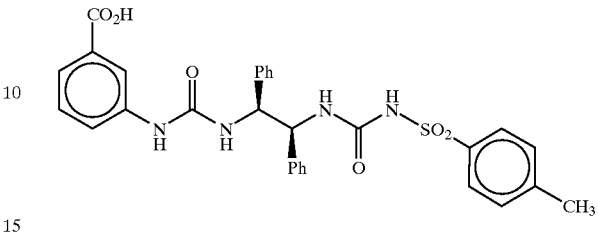

To a solution of ethyl (–)-[S-(R*,R*)]-3-[[[[2-[[[[(4-methylphenyl)sulfonyl]amino]carbonyl]-amino]-1,2-diphenylethyl]amino]carbonyl]amino]benzoate (0.1 g, 0.17 mmol), in MeOH (5 mL) is added lithium hydroxide monohydrate (0.006 g, 0.17 mmol) followed by water to the cloud point. The resulting mixture is warmed to 50° C. for 4 hours. The solvent is removed in vacuo and the residue partitioned between water and diethyl ether. The layers are separated and the aqueous layer is acidified to pH=2 with 2 M HCl. The resulting solid is filtered and dried in vacuo at 114° C. for 5 hours, mp 185–189° C.

IR (KBr): 3383, 1699, 1558, 699 cm$^{-1}$.

NMR (DMSO-d$_6$): δ 2.31 (s, 3H), 4.87–5.04 (m, 2H), 6.84–7.72 (m, 19H), 8.07 (s, 1H), 8.77 (s, 1H), 10.65 (br s, 1H), 12.87 (br s, 1H).

Analysis calculated for C$_{30}$H$_{28}$N$_4$O$_6$S.1.63H$_2$O: C, 59.86; H, 5.23; N, 9.31. Found: C, 59.85; H, 4.96; N, 9.35.

[α]$_D^{25}$=–3.7° (c=1, DMF).

EXAMPLE 68

Ethyl-(–)-[S-(R*,R*)]-3-[[[[2-[[[(4-chlorophenyl)-amino]carbonyl]amino]-1,2-diphenylethyl]amino]-carbonyl]amino]benzoate

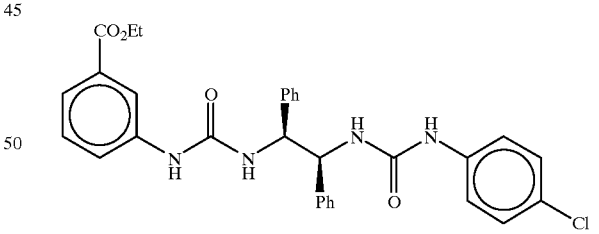

Using Procedure I: Reaction with 4-chlorophenyl isocyanate gives 96% of desired white solid, mp 203–203.5° C.

IR (KBr): 3385, 1653, 1558, 1493, 1238, 700 cm$^{-1}$.

NMR (DMSO-d$_6$): δ 1.30 (t, 3H, J=7.1 Hz), 4.28 (dd, 2H, J=7.1, 14.1 Hz), 5.02 (m, 2H), 6.91–7.59 (m, 19H), 8.10 (s, 1H), 8.77 (s, 1H), 8.92 (s, 1H).

Analysis calculated for C$_{31}$H$_{29}$ClN$_4$O$_4$: C, 66.84; H, 5.25; N, 10.06. Found: C, 66.91; H, 5.45; N, 9.84.

[α]$_D^{25}$=–20.7° (c=1, DMF).

EXAMPLE 69

(−)-[S-(R*,R*)]-3-[[[[2-[[[(4-chlorophenyl)amino]-carbonyl]amino]-31,2-diphenylethyl]amino]carbonyl]-amino]benzoic acid

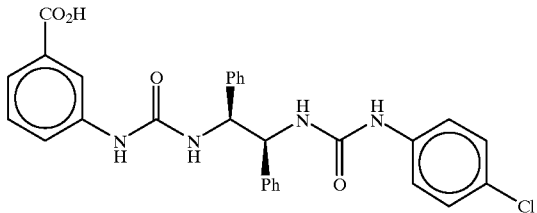

To a solution of ethyl-(−)-[S-(R*,R*)]-3-[[[[2-[[[(4-chlorophenyl)amino]carbonyl]amino]-1,2-diphenylethyl]amino]carbonyl]amino]benzoate (0.15 g, 0.27 mmol) in MeOH (8 mL) is added lithium hydroxide monohydrate (0.01 g, 0.27 mmol) followed by water to the cloud point. The resulting mixture is stirred overnight at room temperature. The mixture is warmed to 50° C. for 3 hours. The solvent is removed in vacuo and the residue partitioned between water and diethyl ether. The layers are separated and the aqueous layer is acidified to pH=2 with 2 M HCl. The resulting solid is filtered and dried in vacuo at 114° C. for 5 hours, mp 172.5–173° C.

IR (KBr): 3383, 1662, 1550, 1493, 1234, 698 cm$^{-1}$.

NMR (DMSO-d$_6$): δ 5.02 (m, 2H), 6.95–7.53 (m, 19H), 8.06 (s, 1H), 8.80 (s, 1H), 8.88 (s, 1H), 12.83 (br s, 1H).

Analysis calculated for $C_{29}H_{25}ClN_4O_4 \cdot 0.5H_2O$: C, 64.74; H, 4.87; N, 10.41. Found: C, 64.57; H, 4.83; N, 10.10.

$[\alpha]_D^{25} = -22.3°$ (c=1, DMF).

EXAMPLE 70

[S-(R*,R*)] and [R-(R*,R*)]-N-(4-nitrophenyl)-N'-1,2-diphenyl-2-[[(phenylamino)carbonyl]amino]ethyl)-urea

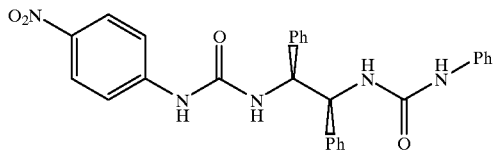

To a solution of [R-(R*,R*)] and [S-(R*,R*)] N-(2-amino-1,2-diphenylethyl)-N'-(4-nitrophenyl)urea (0.1 g, 0.27 mmol) in dichloromethane (10 mL) is added phenyl isocyanate (0.03 g, 0.27 mmol) in one portion. The resulting mixture is stirred 1 hour at room temperature before filtering off the solid product. The product is suspended in hot diethyl ether, filtered, and dried in vacuo at 114° C. for 4 hours, mp 246–247° C.

IR (KBr): 3355, 1656, 1554, 1498, 1330, 1233, 699 cm$^{-1}$;

NMR (DMSO-d$_6$): 5.03 (m, 2H), 6.55–7.37 (m, 17H), 7.59 (d, 2H, J=9.2 Hz), 8.11 (d, 2H, J=9.2 Hz), 8.60 (s, 1H), 9.43 (s, 1H).

Analysis calculated for $C_{28}H_{25}N_5O_4 \cdot 1.0H_2O$: C, 65.49; H, 5.30; N, 13.64. Found: C, 65.44; H, 5.03; N, 13.77.

EXAMPLE 71

[R-(R*,R*)] and [S-(R*,R*)]-4-methyl-N-[[[2-[[[(4-nitrophenyl)amino]carbonyl]amino]-1,2-diphenylethyl]amino]carbonyl-benzenesulfonamide

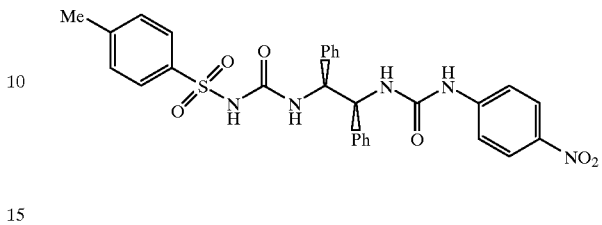

To a solution of [R-(R*,R*)] and [S-(R*,R*)] N-(2-amino-1,2-diphenylethyl)-N'-(4-nitrophenyl)urea (0.1 g, 0.27 mmol) in dichloromethane (10 mL) is added 4-methylbenzenesulfonyl isocyanate (0.05 g, 0.27 mmol) in one portion. The resulting mixture is stirred 1 hour at room temperature before filtering off the solid product. The product is suspended in hot diethyl ether, filtered, and dried in vacuo at 114° C. for 4 hours, mp 223–223.5° C.

IR (KBr): 3367, 1676, 1552, 1498, 1331, 1159, 700 cm$^{-1}$;

NMR (DMSO-d$_6$): 2.32 (s, 3H), 4.95 (m, 2H), 6.97–7.30 (m, 15H), 7.61 (d, 2H, J=9.2 Hz), 7.70 (d, 2H, J=8.2 Hz), 8.15 (d, 2H, J=9.2 Hz), 9.30 (s, 1H).

Analysis calculated for $C_{29}H_{27}N_5O_6S$: C, 60.72; H, 4.74; N, 12.21. Found: C, 60.59; H, 4.65; N, 12.06.

EXAMPLE 72

[S-(R*,R*)] and [R-(R*,R*)]-N-cyclohexyl-N'-[2-[[[(4-nitrophenyl)amino]carbonyl]amino]-1,2-diphenylethyl]urea

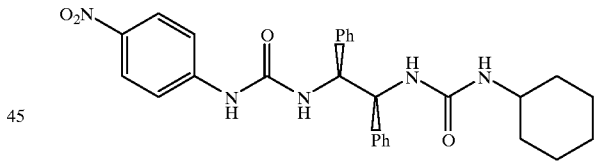

To a solution of [R-(R*,R*)] and [S-(R*,R*)] N-(2-amino-1,2-diphenylethyl)-N'-(4-nitrophenyl)urea (0.1 g, 0.27 mmol) in dichloromethane (10 mL) is added cyclohexyl isocyanate (0.03 g, 0.27 mmol) in one portion. The resulting mixture is stirred 1 hour at room temperature before filtering off the solid product. The product is suspended in hot diethyl ether, filtered, and dried in vacuo at 114° C. for 4 hours, mp 244–245° C.

IR (KBr): 3337, 2931, 1639, 1559, 1507, 1330, 700 cm$^{-1}$;

NMR (DMSO-d$_6$): 0.97–1.66 (rn, 10H), 4.94 (m, 2H), 5.94 (d, 1H, J=7.5 Hz), 6.42 (d, 1H, J=7.5 Hz), 7.03–7.19 (m, 12H), 7.60 (d, 2H, J=9.2 Hz), 8.12 (d, 2H, J=9.2 Hz), 9.51 (s, 1H).

Analysis calculated for $C_{28}H_{31}N_5O_4$: C, 67.05; H, 6.23; N, 13.96. Found: C, 66.74; H, 6.22; N, 13.98.

EXAMPLE 73

[R-(R*,S*)]-N-(4-chlorophenyl)-N'-(2-hydroxy-1,2-diphenylethyl)urea

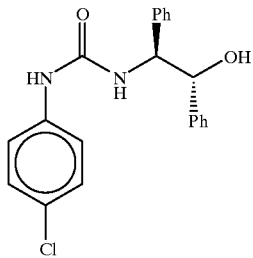

To a solution of (−)-[R-(R*,S*)]-2-amino-1,2-diphenylethanol (1.0 g, 4.7 mmol) in dichloromethane (10 mL) is added dropwise a solution of 4-chlorophenyl isocyanate (0.72 g, 4.7 mmol) in dichloromethane (5 mL). The resulting mixture is stirred 1 hour at room temperature before filtering off the solid product and washing with $CH_2Cl_2$ (2×). The product is dried in vacuo at 114° C. to provide 1.4 g (81%) of desired product, mp 198° C.

IR (KBr): 3327, 1665, 1549, 1234, 703 cm$^{-1}$;

NMR (DMSO-d$_6$): 4.95 (m, 1H), 5.74 (m, 1H), 6.84–7.5 (m, 16H, 8.84 (S, 1H).

Analysis calculated for $C_{21}H_{19}ClN_2O_2 \cdot 0.42H_2O$: C, 67.37; H, 5.34; N, 7.48. Found: C, 67.36; H, 5.16; N, 7.61.

What is claimed is:

1. A compound of formula

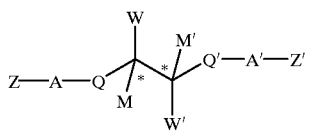

I or a pharmaceutically acceptable salt thereof wherein:
Z and Z' are each independently selected from:
  hydrogen,
  CN,
  alkyl of from 1 to 6 carbon atoms,
  branched alkyl of from 3 to 9 carbon atoms,
  cycloalkyl or polycycloalkyl of from 5 to 12 carbon atoms unsubstituted, mono- or disubstituted with one 6r more substituents selected from:
    alkyl,
    branched allyl,
    $CO_2R^1$, and
    —$OR^3$ wherein $R^1$ is as defined below, and
  $R^3$ is
    hydrogen,
    —$CH_3$,
    —$CH_2CH_3$, or
    $C(O)CH_3$;
  unsubstituted, mono- or polysubstituted phenyl, polyaromatic, heteroaromatic, or hydroaromatic which substituents are selected from:
    alkyl of from 1 to 6 carbon atoms,
    branched allyl of from 3 to 9 carbon atoms,
    hydrogen,
    —CN,
    —F,
    —Cl,
    —Br,
    —I,
    —$NO_2$,
    —$CF_3$,
    —SMe,
    —$S(O)_2CF_3$,
    —S(O)Me,
    —$S(O)_2Me$,
    —$(CH_2)_mS(O)_2OR^1$,
    —$S(O)_2NR^1R^2$,
    —CHO,
    —C(NOH)H,
    —$(CH_2)_mCO_2R^1$,
    —$C(O)NR^1R^2$,
    —$NR^1R^2$,
    —$C(O)CO_2R^1$,
    —$C(NOH)CO_2R^1$,
    —$OR^1$,
    —OAc,

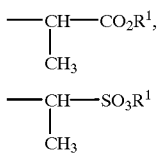

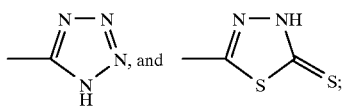

A' is

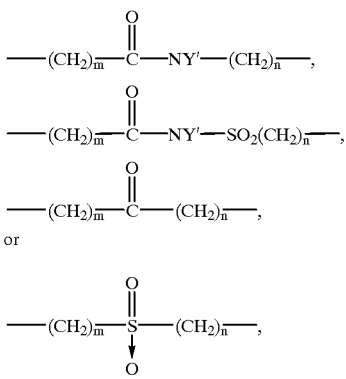

A' is a bond,

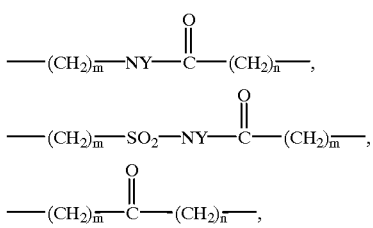

-continued

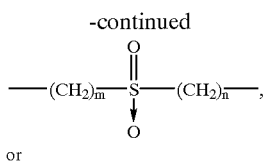

or

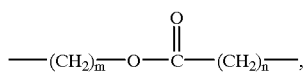

Q and Q' are each independently NY, NY' wherein Y and Y' are each independently:
hydrogen,
phenyl,
benzyl,
straight alkyl of from 1 to 4 carbon atoms,
branched alkyl of 3 or 4 carbon atoms,
—(CH$_2$)$_n$CO$_2$R$^1$, or
—(CH$_2$)$_n$—C(O)NR$^1$R$^2$;

W and W' are each independently:
phenyl which is unsubstituted, mono- or polysubstituted by:
hydrogen,
—CN,
—SMe,
—SO$_2$CF$_3$,
—S(O)Me,
—S(O)$_2$Me,
—(CH$_2$)$_m$S(O)$_2$OR$^1$,
—S(O)$_2$NR$^1$R$^2$,
—CHO,
—C(NOH)H,
—(CH$_2$)$_m$CO$_2$R$^1$,
—C(O)NR$^1$R$^2$,
—NR$^1$R$^2$,
—(CO)CO$_2$R$^1$,
—C(NOH)CO$_2$R$^1$,
—OR$^1$,
—OAc,
—F,
—Br,
—Cl,
—I,
—CF$_3$,
—NO$_2$,
alkyl of from 1 to 6 carbon atoms,
branched alkyl of from 3 to 9 carbon atoms,

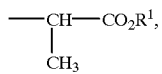

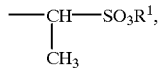

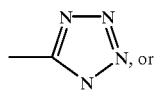  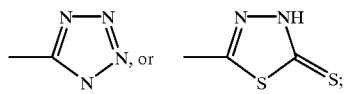

also, W and W' are each independently:

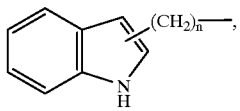

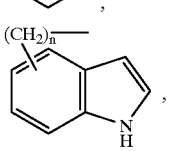

cyclo or polycycloalkyl unsubstituted or substituted by one or more selected from alkyl, CO$_2$R$^1$, and —S(O)$_2$OR$^1$,
M and M' are each independently hydrogen, methyl, or fluorine,
R$^1$ and R$^2$ are each independently hydrogen or lower alkyl;
with the proviso that at least one urea or sulfonylurea is present and at least one heterocycle is present.

2. A compound according to claim 1 wherein:
Z and Z' are each independently selected from;
hydrogen,
cyclo- or polycycloalkyl of from 5 to 12 carbon atoms unsubstituted, mono- or disubstituted with substituents selected from:
alkyl,
CO$_2$R$^1$, or
—OR$^3$ wherein R$^3$ is
hydrogen,
CH$_3$,
CH$_2$CH$_3$, or
C(O)CH$_3$;
unsubstituted, mono- or disubstituted phenyl which substituents are selected from:
hydrogen,
—CN,
—SMe,
—S(O)Me,
—S(O)$_2$Me,
—Cl,
—Br,
—F,
—I,
—CF$_3$,
—NO$_2$,
alkyl of from 1 to 6 carbon atoms,
branched alkyl of from 3 to 9 carbon atoms,
—(CH$_2$)$_m$S(O)$_2$OR$^1$,
SO$_2$CF$_3$,
SO$_2$NR$^1$R$^2$, CHO,
—C(NOH)H,
—(CH$_2$)$_m$CO$_2$R$^1$,
—C(O)NR$^1$R$^2$,
—NR$^1$R$^2$,
—C(O)CO$_2$R$^1$,
—(NOH)CO$_2$R$^1$,
—OR$^1$,
—OAc,

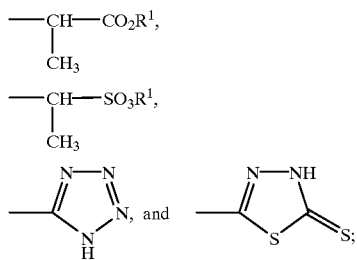

wherein R' and R$^2$ are each independently hydrogen or lower alkyl,
wherein in A' m is from 0 to 1 and independently n is from 0 to 1;
Q and Q' are each independently NY, NY' wherein Y and Y' are each independently:
hydrogen,
methyl,
benzyl,
isopropyl,
isobutyl,
sec-butyl,
—CH$_2$CO$_2$R$^1$, or
—CH$_2$C(O)NR$^1$R$^2$,
W and W' are each independently;
phenyl which is unsubstituted, mono- or polysubstituted by:
chlorine,
—CF$_3$,
fluorine,
—NO$_2$,
—CO$_2$R$^1$,
bromine,
—SO$_3$H,
—SO$_2$NH$_2$;
also, W and W' are independently:

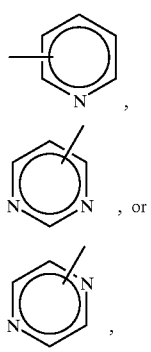

M and M' are each independently H, Me, or F.

3. A compound of formula I

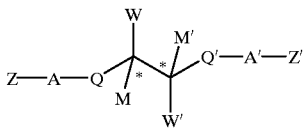

wherein
Z and Z' are each independently:
4-chlorophenyl,
4-(trifluoromethyl)phenyl,
4-nitrophenyl,
4-methylphenyl,
4-methoxyphenyl,
4-fluorophenyl,
4-cyanophenyl,
4-methylthiophenyl,
4-(methylsulfonyl)phenyl),
phenyl,
cyclohexyl, or
2-adamantyl;
A' is:

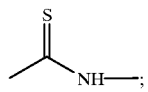

A is:

Q and Q' are each independently NY and NY';
Y and Y' are each independently hydrogen or methyl;
W and W' are each independently phenyl, -3-chlorophenyl or 2-chlorophenyl, and
M and M' are each H.

4. A compound of formula

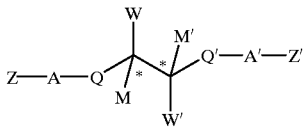

or a pharmaceutically acceptable salt thereof wherein:
Z and Z' are each independently selected from:
hydrogen,
CN,
alkyl of from 1 to 6 carbon atoms,
branched alkyl of from 3 to 9 carbon atoms,
cycloalkyl or polycycloalkyl of from 5 to 12 carbon atoms unsubstituted, mono- or disubstituted with one or more substituents selected from:
alkyl,
branched alkyl,
CO$_2$R$^1$, and
—OR$^3$ wherein R$^1$ is as defined below, and
R$^3$ is hydrogen,
—CH$_3$,
—CH$_2$CH$_3$, or
C(O)CH$_3$;

unsubstituted, mono- or polysubstituted phenyl, polyaromatic, heteroaromatic, or hydroaromatic which substituents are selected from:
alkyl of from 1 to 6 carbon atoms,
branched alkyl of from 3 to 9 carbon atoms,
hydrogen,
—CN,
—F,
—Cl,
—Br,
—I,
—NO$_2$,
—CF$_3$,
—SMe,
—S(O)$_2$CF$_3$,
—S(O)Me,
—S(O)$_2$Me,
—(CH$_2$)$_m$S(O)$_2$OR$^1$,
—S(O)$_2$NR$^1$R$^2$,
—CHO,
—C(NOH)H,
—(CH$_2$)$_m$CO$_2$R$^1$,
—C(O)NR$^1$R$^2$,
—NR$^1$R$^2$,
—C(O)CO$_2$R$^1$,
—C(NOH)CO$_2$R$^1$,
—OR$^1$,
—OAc,

—CH(CH$_3$)—CO$_2$R$^1$,   —CH(CH$_3$)—SO$_3$R$^1$,

A' is

—C(O)—NY'—(CH$_2$)$_n$—,

—C(S)—NY'—(CH$_2$)$_n$—,

—C(O)—NY'—SO$_2$(CH$_2$)$_n$—,

—C(S)—NY'SO$_2$—(CH$_2$)$_n$—, wherein n is 0–3;

A is

—(CH$_2$)$_m$—NY—C(O)—,

—(CH$_2$)$_m$—NY—C(S)—,

—(CH$_2$)$_m$—SO$_2$—NY—C(O)—, and

-continued

—(CH$_2$)$_m$—SO$_2$NY—C(S)—, wherein m is an integer of 0–3;

Q and Q' are each independently NY, NY' wherein Y and Y' are each independently:
hydrogen,
phenyl,
benzyl,
straight alkyl of from 1 to 4 carbon atoms,
branched alkyl of 3 or 4 carbon atoms,
—(CH$_2$)$_n$CO$_2$R$^1$, or
—(CH$_2$)$_n$—C(O)NR$^1$R$^2$;

W and W' are each independently:
phenyl which is unsubstituted, mono- or polysubstituted by,
hydrogen,
—CN,
—SMe,
—SO$_2$CF$_3$,
—S(O)Me,
—S(O)$_2$Me,
—(CH$_2$)$_m$S(O)$_2$OR$^1$,
—S(O)$_2$NR$^1$R$^2$,
—CHO,
—C(NOH)H,
—(CH$_2$)$_m$CO$_2$R$^1$,
—C(O)NR$^1$R$^2$,
—NR$^1$R$^2$,
—(CO)CO$_2$R$^1$,
—C(NOH)CO$_2$R$^1$,
—OR$^1$,
—OAc,
—F,
—Br,
—Cl,
—I,
—CF$_3$,
—NO$_2$,
alkyl of from 1 to 6 carbon atoms,
branched alkyl of from 3 to 9 carbon atoms,

—CH(CH$_3$)—CO$_2$R$^1$,

—CH(CH$_3$)—SO$_3$R$^1$, tetrazolyl, or thiadiazole-thione;

also, W and W' are each independently:

indolyl-(CH$_2$)$_n$—,

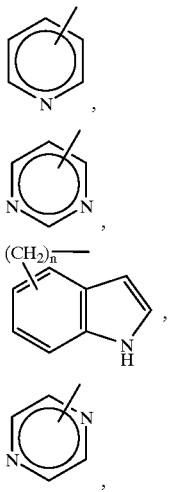

cyclo or polycycloalkyl unsubstituted or substituted by one or more selected from alkyl, $CO_2R^1$, and $-S(O)_2OR^1$;

M and M' are each independently hydrogen, methyl, or fluorine;

$R^1$ and $R^2$ are each independently hydrogen or lower alkyl with the proviso that at least one thiourea is present.

5. A method of suppressing appetite which comprises administering to a mammal in need of said treatment a therapeutically effective amount of a compound according to claims 1, 3 and 4.

6. A method of reducing gastric acid secretion which comprises administering to a mammal in need of said treatment a therapeutically effective amount of a compound according to claims 1, 3 and 4.

7. A method of treating anxiety which comprises administering to a mammal in need of said treatment a therapeutically effective amount of a compound according to claims 1, 3 and 4.

8. A method of treating gastrointestinal ulcers which comprises administering to a mammal in need of said treatment a therapeutically effective amount of a compound according to claims 1, 3 and 4.

9. A method of treating psychosis which comprises administering to a mammal in need of said treatment a therapeutically effective amount of a compound according to claims 1, 3 and 4.

10. A method of treating schizophrenia which comprises administering to a mammal in need of said treatment a therapeutically effective amount of a compound according to claims 1, 3 and 4.

11. A method of treating the withdrawal response produced by chronic treatment or abuse of drugs or alcohol in a mammal in need of such treatment which comprises a therapeutically effective amount of a compound according to claims 1, 3 and 4.

12. A compound selected from:

[S-(*,R*)] and [R-(R*,R*)]-N-[2-[[[(4-cyanophenyl)amino]thioxomethyl]amino]-1,2-diphenylethyl]-N'-[4-(trifluoromethyl)phenyl]urea;

[R-(R*,R*)] and [S-(R*,R*)]-N-[1,2-diphenyl-2-[[[(phenylmethyl)amino]thioxomethyl]-amino]ethyl]-N'-[4-(trifluoromethyl)phenyl]urea; and

[S-(R*,R*)] and [R-(R*,R*)]-N-[1,2-diphenyl-2-[[[(phenylamino)thioxomethyl]amino]-ethyl]-N'-[4-(trifluoromethyl)phenyl]urea.

13. A pharmaceutical composition comprising an effective amount of a compound according to claims 1, 3 and 4 in combination with a pharmaceutically acceptable carrier effective for appetite suppression, for reducing gastric acid secretion, for reducing anxiety, for treating gastrointestinal ulcers, for treating psychosis, for treating schizophrenia, and for preventing the withdrawal response produced by chronic treatment or abuse of drugs or alcohol in unit dosage form.

* * * * *